US007122721B1

(12) United States Patent
Duwenig et al.

(10) Patent No.: US 7,122,721 B1
(45) Date of Patent: Oct. 17, 2006

(54) PLANT GENE EXPRESSION UNDER THE CONTROL OF CONSTITUTIVE PLANT V-ATPASE PROMOTERS

(75) Inventors: Elke Duwenig, Freiburg (DE); Thomas Rausch, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 69 days.

(21) Appl. No.: 09/636,826

(22) Filed: Aug. 14, 2000

Related U.S. Application Data

(60) Provisional application No. 60/157,887, filed on Oct. 5, 1999.

(51) Int. Cl.
*C12N 15/82* (2006.01)
*A01H 5/00* (2006.01)

(52) U.S. Cl. ............... 800/287; 800/298; 536/24.1; 435/320.1; 435/419; 435/468; 435/252.3; 435/69.1; 435/430

(58) Field of Classification Search ........... 435/320.1, 435/419, 468, 252.3, 71.1; 536/24.1; 800/278, 800/289, 298
See application file for complete search history.

(56) References Cited

U.S. PATENT DOCUMENTS

| 5,641,876 A | 6/1997 | McElroy et al. ........... 536/24 |
| 5,753,475 A | 5/1998 | Houck ..................... 435/172 |

FOREIGN PATENT DOCUMENTS

| EP | 337 532 | 10/1989 |
| EP | 426 641 | 5/1991 |
| EP | 559 603 | 9/1993 |
| WO | WO 91/05054 | 4/1991 |
| WO | WO 91/13991 | 9/1991 |
| WO | WO 93/07279 | 4/1993 |
| WO | WO 94/21793 | 9/1994 |
| WO | WO 95/19443 | 7/1995 |
| WO | WO 96/07746 | 3/1996 |
| WO | WO 96/12814 | 5/1996 |
| WO | WO 97/20058 | 6/1997 |
| WO | WO 97/27307 | 7/1997 |
| WO | WO 99/00492 | 1/1999 |
| WO | WO 99/09190 | 2/1999 |

OTHER PUBLICATIONS

Struve et al. Structure and function of the promoter of the carrot V-type H(+)-ATPase catalytic subunit gene. J Biol Chem. 1990 May 15;265(14):7927-32.*
Acuto S. et al. An element upstream from the human delta-globin-encoding gene specifically enhances beta-globin reporter gene expression in murine erythroleukemia cells. Gene. Feb. 12, 1996;168(2):237-41.*
Becker N.A. et al. Characteristions of a polypurine/polypyrimidine sequence upstream of the mouse metallothionein-1 gene. Nucleic Acids Res. Apr. 15, 1988;26(8):1951-8.*
Yanaka N. et al. Isolation and characterization of the 5'-flanking regulatory region of the human natriuretuc peptide receptor C gene. Endocrinology. Mar. 1998;139(3);1389-400.*
Maiti A.K. et al. Poly purine.pyrimidine sequences upstream of the beta-galactosidase gene affect gene expression in *Saccharomyces cerevisiae*. BMC Mol Biol. 2001;2(1):11. Epub Oct. 8, 2001.*
Ward et al. "Chemical regulation of transgene expression in plants" Plant Molecular Biology, vol. 22 (1993) pp. 361-366.
Fluhr et al. "Organ-Specific and Light-Induced Expression of Plant Genes" Science, vol. 232 (1986) pp. 1106-1112.
Edwards et al. "Cell-Specific Gene Expression in Plants" Annu. Rev. Genet. vol. 24 (1990) pp. 275-303.
Schmülling et al. "Promoters of the rolA, B, and C Genes of *Agrobacterium rhizogenes* Are differently Regulated in Transgenic Plants" The Plant Cell vol. 1 (1989) pp. 665-670.
Ito et al. "Meristem-specific gene expression direted by the promoter of the S-Phase specific gene cyc07, in transgenic *Arabidopsis*" Plant Molecular Biology vol. 24 (1994) pp. 863-878.
Franck et al. "Nucleotide Sequence of Cauliflower Mosaic Virus DNA" Cell vol. 21 (1980) pp. 285-294.
Benfey et al. "The CaMV 35S enhancer contains at least two domains which can confer different developmental and tissue-specific expression patterns" The EMBO Journal vol. 8 (1989) pp. 2195-2202.
McElroy et al. "Isolation of an Efficient Actin Promoter for Use in Rice Transformation" the Plant Cell vol. 2 (1990) pp. 163-171.
Klink et al. "Membrane Particles, Protein and ATPase Activity of Tonoplast Vesicles of *Mesembryanthemum crystallinum* in the C-3 and CAM state" Botanica Acta vol. 103 (1990) pp. 24-31.
Fischer-Schliebs et al. "Differential Immunology Cross-Reactions with Antisera against the V-ATPase of *Kalanchoë diagremontiana* Reveal Structural Differences of V-ATPase Subunits of Different Plant Species" Biol. Chem. vol. 378 (1997) pp. 1131-1139.
Rausch et al. "Salt Stress Responses of Higher Plants: The Role Proton Pumps and $Na^+/H^+$-Antiporters" J. Plant Physiol. vol 148 (1996) pp. 425-433.

(Continued)

*Primary Examiner*—Cynthia Collins
(74) *Attorney, Agent, or Firm*—Novak Druce & Quigg LLP

(57) ABSTRACT

To express selection genes and resistance genes, it would be desirable to have available plant constitutive promoters which has a strong uniform constitutive activity in as many plant tissues or cell types as possible and which, moreover, show an even stronger activity, or are not repressed, under stress conditions. The invention provides DNA constructs which encompass a plant V-ATPase promoter which is operatively linked with a heterologous gene. The invention furthermore relates to the use of these constructs in the form of expression cassettes, recombinant vectors and in transgenic plants, plant cells or protoplasts. In particular the invention relates to the promoter of the *Beta vulgaris* V-ATPase subunit c isoform 2.

37 Claims, 10 Drawing Sheets

OTHER PUBLICATIONS

Löw et al. "Early Salt Stress Effects on the Differential Expressio of Vacuolar $H^+$-ATPase Genes in Roots and Leaves of *Mesembyranthemum crystallinum*[1]" Plant Physiol. vol. 110 (1996) pp. 259-265.

Löw. et al. "In suspension-cultured *Daucus carota* cells salt stress stimulates $H^{30}$-transport but not ATP hydrolysis of the V-ATPase" Journal of Experimental Botany vol. 47 (1996) pp. 1725-1732.

Lehr et al. "cDNA and genomic cloning of sugar beet V-type $H^+$-ATPaase subunit A and c isoforms: evidence for coordinate expression during plant development and coodinate induction in response to high salinity" Plant Molecular Biology vol. 39, (1999) pp. 463-475.

Kirsch et al. "Salt stress induces and increased expression of V-type $H^+$-ATPase in mature sugar beet leaves" Plant Molecular Biology vol. 32 (1996) pp. 543-547.

* cited by examiner

V-ATPase su A

V-ATPase su $c_1$

V-ATPase su $c_2$ co  +NaCl

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 2090 nucleic acids
      (B) TYPE: nucleic acid
      (C) STRANDEDNESS: single
      (D) TOPOLOGY: linear (xi) SEQUENCE DESCRIPTION: SEQ ID NO: 1:

```
GATATCACAC ATTCGTCCAT CGACGATTTG CGAACTTTCA AATAGGTACG TAATTCTTTT      60

AATCTTCAAA GTTATTTCAC ATTAGTCGAC TATTATGTAG TTGAAAAAAT GGAGATAATA     120

GGAATTAGTT GAAAAGGGTG TTTATATAAT TAGACTTAAA TTTGATTCAT TTTCATATAT     180

CTGAAAACAA GGTATGTATG AAATTTGATT CATTTATGAC ACTGATGAAA AAGTTAACGA     240

TTTAGTTCTT TTTTTTAAAA TTCCAATATA AATTTTTGCC CAAAACTTTT GCAAAATATC     300

CATGTTCGGA ATAAATTTT GAAAACAAA ACAATATCAA ACCTTTTTGC GAACAACTTT      360

TACAAAAATC CATTTTCAGA AAAAAAAATT TACATTAACT TGCGAAATCA AATTGTGTAT     420

GAAAAATTTA AATTTCCTT TCACCTATAA TTGAAACTCA AAGTGTTAAA ATTTAGAAAA     480

GGAGAAAAAT AAAAAATGAC CATTTCATGC GAAATCAAAT TGTGTATGAA AAACTTAAAA     540

TTTTATTTTA AATATAATTG AAATTCAAAG TGTTAAAATT TAGAAAAGGA GAAAAATTAA     600

AATGACCATT TCATTCAAAA TCAGATTGTG TATGAAAAAT TTAAATTTTT ATTTCAAATA     660

TAATTGAAAC TCAAAGTGTG AACATTTAGA AAAGGAGAAA AATTAAAATG ATGAAAATTT     720

GTAAAACATC AATTTGTGAA ATCAGAATTT AGAAGTTAGA CAAGGAAAAA AAACTGAATT     780

GTCTTATACT TTTCGGTTAC AATTTTGGGA TCATAAAGAA ATTACTGAAA TCCATATCAA     840

AAACTATTAT AAATTACAAA AATGAATAAA ACCAAAAAAA GAAGAACATG ACGATATTTC     900

GTAAAGAACA TCATACTGAT TATAAAAGAA CATGCGCATA TTAGAATTGA GAAACAAAAA     960

ACTATTCAAA ATCACAAAAA TGGATAACAA CATACAAAGA ACATGAAAGA ATCTTATTCA    1020

CAAAATGGAG GTGAACTTAA ATACTAACTT GCATTTTCAG TTTATTTACT ACTTAGTATT    1080

AGGCCTAAAA ATATCATCGC ACGCATCGCG TGCACAAAAG ACTAGTGTTA AGTATCACAA    1140

GTCACAAACT CACAACTGAT TTTCATTTAG GCTCCATTTG GTAGGGCGTA AAACGTTTTC    1200

CCGGAACACT ATTTTTCTCC ATTTTTAGTT TTACATTGTT TGGTTGACAA AAGAGTGTAA    1260

AACCGTTTTC CCTTGGGGTA AAATTACTCT TCCAATGATC GAAAACCATT TTCCTTTCAA    1320

AATGAAGGGA AAACTGTTTT CCTTATCTCT CTTGTTACAC TTTTCTCACT ACCTCCTTAC    1380

TTTCCCTTTT ATTTTACTTT CATTTCATCA TTTTCTTTGC ATGAAACCAA ACAACGGAAA    1440

ACTAATTTTG GAATTGTGTT TTCCATTGTA AATTGTTTTC CATGAAAATC ATTTTACACT    1500

GAAAATGTTT TACACCCTAC CAAACAGAGC CTTCGTGTGC CATGAATGCA TGACCGATTT    1560

CAAATTCGAA ACTGGTGTTT ACCGTTTCCT AATTGGTTTC GAGTTCACAA CCAAGTATTC    1620

AACTATGTTG CTCACCCTAA AGATGAATAT GGTAAAACCT TGAGGTGGGC TTTGGCTAAA    1680

AAAGTCCCA CCAAGCCCCA ATTCTAGGCT CCCAAAACCA CGAAATTCC TGGTACTATT      1740

CCAAAACAAA AACAAACACC TCCTGATCAA ACCAGAAAAA ATAAAACATA TTTTTGTTTT    1800

CTCCCAATTT TTCATTTTAA TTTATCACGG GAAAGTACAC AATAATTCAA TCAAGGGTAA    1860

AAAAAATAAA ATAAAAAGAA AAGATAAGTA TAAACAAAAG AAATTTGTCT TCTCTACATC    1920

CTCATATTTC ATCCACGCTC TCTTCTTCCT CTCCTCTCAT CTCCTTTTTC AATTCCCAGA    1980

TCGGATCAAG CAATTCATCG AACACCTTCC GATCATCACC ATCAAAAAAA ATGTCAACAG    2040

TCTTTAACGG CGATGAAACG GCGCCGTTCT TCGGCTTTCT GGGTGCTGCT                2090
```

(2) INFORMATION FOR SEQ ID NO: 2:

(i) SEQUENCE CHARACTERISTICS:
        (A) LENGTH: 1153 nucleic acids
        (B) TYPE: nucleic acid
        (D) TOPOLOGY: linear (xi) SEQUENCE DESCRIPTION: SEQ ID NO: 2:

```
GGGTGGGGGT GAAGTGGGGG CTGCAGGGGT GGGTGGGGGG GGCTGGTGGC AGGTATTGGT      60
AGTGGTGCTA GGTGGTGATT ATGGAGGAAG AAGGGAAATA GAAGTGGTTA ACACCGAAAA     120
GTGAGATTAA GTTTTATCTT GCAAAAATAA TTTATTTTTT GGTTTGTTTT CACAAAGAAT     180
GCTTTATTAA GGTTTTTTTT TGCAAAAAAC TGAACTTTTA AAAGGTTTTT TTTGATAAAT     240
TTTCCTAATA TTAATAAATG AAAATTTTTC TAACATGGGA GATAGCCTGG ACCTATAACT     300
AGTTGTTATA ACTTATAAGA AGAGAATTTT GGGCAACTAT GCGGAAAATA GGGGAAATTT     360
TGGAAAAAAT AAGTAAAAGA TTTTAGGTGT AAACTTGCTT GTTATAAGTT ATAAACTTGA     420
ATTTGTTCTA TTGATAGTGT TGGTTAATAA TGTGACAACT AAATCGAACA TAAAGGTTTA     480
GGACCCTTTC GACATCATTG AGAGTTAGAG GTGGGCATGA GCCGGCCAG TTCGCGTGCT      540
GGAACGGCCA GTTCGCGGGC TGGTACGGCC AGGCACGAGC CCGATCAAGG CACGACCCGG     600
CTTGTTGTCC GCTACGTGGA CCGTGGGCCC ATCACGGTCA AAAAAAAATA TTTTAGGCTC     660
GCACCAGCAC GAGCCCGCGT AGGCCAGCCC GCGGGCTGAA TGTTCCTTTC CTTTGTTTTT     720
TAGCCTAAAA CTGTCATAAA TACAAAAAGA TAACATAAAA CACAGGCTAG GCCCTCAATA     780
GGCACGAGCC CGTGGAAAAA ATCCGAAAAT TCCAAGCCTA GCTAGTTACT CACAAGCTCA     840
GACCCGATTC GTCATTTTTC CAAACCCGTG GGCCGAGCCG GTGAACAGGC TCGGCCCGGC     900
TCATGTCCAG GTGACAGGTC TACTGAGAGT TATGAGTTGT TTCCCCATGG GCTACTTGAC     960
TACAAACCTT CCATAGTTCC ATGACACTTC CATCTGAGCC CATGAGATAA AATTAAGGAA    1020
TACAAACACA AAACTCAACA ACCAACCCGA AATATCGATC GGACTTGTTA GCACGTGTTA    1080
TGTTGGGTCC CATCCAAGAA ACTTTCTCTC TCCTCCTCCT TCATAAAAAA ACCTTCTCAC    1140
TGATCCCATC CAG                                                     1153
```

(2) INFORMATION FOR SEQ ID NO: 3:

(i) SEQUENCE CHARACTERISTICS:
        (A) LENGTH: 1073 ???? acids
        (B) TYPE: nucleic acid
        (D) TOPOLOGY: linear (xi) SEQUENCE DESCRIPTION: SEQ ID NO: 3:

```
GAATTCTCTG CTCTGGATTC GACATCAAAA TTTCCACCGG GTTACTATTC AAACAGACTG      60
CTCAAATCTC ATTTCTTCTC TTCGTTCTAT TTCGACGGTG CCTCGCTCTA TCTACTGGTC     120
TGTATGCCAG ATTATGAGTC TAACAGGAAA TCTTCACTGG TGTTTTCTGC TTAAAGTAAA     180
TTGTCAAAAA GTTCAAAAGG CACAAAATGT GGCTAAGCTA TGTGCTCAAA TTTGTTGTTT     240
ACTACTTGAT TTGTTTTCTT TCTCTTTATG CCTGTTTTTT CCCCCTTTGT AAAAAAAAGA     300
TACAAGTATA GATGAAGGGA TTCTTTATAT TGGCCCCATG TGTTCGTTAG ATAATTACAT     360
TGTACCCTCA ATTCCTCATC TTCCTTGAAG TTCTACGTAG TACCATTGTG GTTGCATAAG     420
CAAATGATAA TCATACTTTC ATATCTTAGT TAATGTACAT CGTCACTTGT GCTTAACATG     480
TCATAAACTA ATTTCCTTGG TTTAATACTG GTTACATTAA CTAAATCTTT TATTCTTAAA     540
TATTTAAGAA GTGTGCAGTA AATTAAGTTT CTTCCAAATC CTCAATAAGA CATTATACTT     600
```

-continued

| | | | | | |
|---|---|---|---|---|---|
| AGAAAACTTC | TATAAAGTTA | CTTATCAACT | TACAGATAAC | GACCAAAGAA | TCATCACCAA | 660 |
| AACAGTTATC | GAACCACATA | GAAGCTGCAT | AGCTTTTGAA | AAAGGTGAAG | GTACAATATA | 720 |
| AATCTCCAAC | AAATATAGTG | TATCTACTCC | CAAAAGCTAT | CCTAGTAATA | TCCCTATCTC | 780 |
| AAAAACATAT | CTTTTATCAA | CTTTTTCCCA | ACACAAACTC | AATTGTTAAA | AACTACAAGG | 840 |
| AAACGTTGTT | TAACCAATCA | CTATATTTAC | ATTAACCATA | TTTTTAATTT | AGTTAAACCT | 900 |
| CTCAAGTCTC | ACTACATTCT | TAAAAAAAGT | TGGAGATAGA | GTCATCATAA | TTCATAGAGA | 960 |
| AGGAATTGAC | AACATCTAAT | AAGAACGAAT | TACGAACGTG | GCAAAATCAC | AGACGAAACA | 1020 |
| TAGCAAAACT | TAACCCTGCA | AATCTCAATC | AGATTTAAAT | AATCCTTTTG | CTG | 1073 |

PLANT GENE EXPRESSION UNDER THE CONTROL OF CONSTITUTIVE PLANT V-ATPASE PROMOTERS

This application claims the benefit of U.S. Provisional Application No. 60/157,887, filed Oct. 5, 1999.

Plant gene expression under the control of constitutive plant V-ATPase promoters.

The invention relates to DNA constructs which encompass a plant V-ATPase promoter which is operatively linked to a heterologous gene. The invention furthermore relates to the use of these constructs in the form of expression cassettes, recombinant vectors and in transgenic plants, plant cells or protoplasts. In particular, the invention relates to the promoter of *Beta vulgaris* V-ATPase subunit c isoform 2.

Genetic engineering methods allow foreign genes to be transferred specifically into the genome of a plant. This process is termed transformation, and the resulting plants are termed transgenic plants. When expressing foreign genes in plants, the choice of the promoter is frequently a critical factor. While it may be desirable to express a gene only as the response to a particular abiotic or biotic stimulus or to localized expression in a specific tissue, other genes should preferably be expressed constitutively, i.e. in the entire plant at all times and in all tissues.

Examples for expression which can be induced by a particular stimulus are the wound induction, which is described, for example, in WO 93/07279 and, for potatoes, in EP 0 375 091 A1, or chemical induction, which has been described in WO 95/19443 (Ward et al. (1993) Plant Molecular Biology 22, 361–366), such as, for example, the induction with salicylate, which is known from EP 0 337 532 B1, or light induction (Fluhr et al. (1986) Science 232, 1106–1112 and WO 91/05054), and temperature-dependent induction, also described in EP 0 337 532 B1 and, for tomatoes, in WO 96/12814.

Examples of cell- and tissue-specific expression are seed-, tuber- and fruit-specific expression (see review by Edwards and Coruzzi (1990) Annu. Rev. Genet. 24, 275–303 and U.S. Pat. No. 5,753,475).

Phloem-specific expression (Schmülling et al. (1989) Plant Cell 1, 665–670), root-nodule-specific expression (DE 3702497) and meristem-specific expression (Ito et al. (1994) Plant Molecular Biology 24, 863–878) are also known.

Promoters which cause constitutive expression of the genes controlled by them can be employed, for example, for selecting transformed plant cells (expression of a selectable marker gene in transgenic plants, generation of antibiotic-resistant plant cells) or for generating herbicide-tolerant, insecticide-tolerant and pathogen-stress-resistant plants, since the products of the genes controlled by them are present in all parts of the plant.

Foreign genes of other agronomic, medicinal or other importance can be expressed in a variety of plants, for example for generating heterologous recombinant proteins and for generating plants which contain mammalian polypeptides. The quantity of the expression pattern over space and time, of endogenous plant genes, can also be advantageously altered with the aid of constitutively active promoters.

The constitutive promoter which is most frequently used in plant genetics is the viral 35S CaMV promoter (Franck et al. (1980) Cell 21, 285–294). This promoter contains different recognition sequences for transcriptional effectors which, in their totality, result in constitutive expression of the gene which has been introduced (Benfey et al. (1989) EMBO J. 8, 2195–2202).

Other constitutive promoters of viral origin are, for example, the fig-wort mosaic virus promoter, which has been described in EP 0 426 641, the Australian banana-infecting badnavirus (WO 99/00492) and the sugar cane bacilliform virus promoter described in WO 99/09190.

Plant-intrinsic constitutive promoters are, for example, the maize ALS promoter (WO 96/07746), the rice actinl promoter (McElroy et al., Plant Cell 2, 163–171, 1990, U.S. Pat. No. 5,641,876), the wheat proline-rich protein promoter described in WO 91/13991, the raspberry DRU promoter (WO 97/27307) and the *Medicago sativa* H3 histone promoter (WO 97/20058).

To express selection genes and resistance genes, it would be desirable to have available promoters which show a strong, uniform constitutive activity in, if possible, all plant tissues or cell types and which, moreover, show even greater activity, or are not repressed, under stress conditions. Advantageously, these promoters should not be derived from plant pathogens (as is the 35S CaMV promoter), whose expression might also differ in different plant tissues.

Regulation of the constitutive 35S promoter by stress factors has not been described (frequently, elements of other stress-inducible promoters are coupled to the CaMV 35S promoter); most of the stress-induced promoters show a virtually undetectable expression under normal conditions (which is a disadvantage) and are only strongly induced under the respective inducing stress conditions. They are therefore unsuitable for many uses.

WO 94/21793 describes a constitutive promoter which is modulated by environmental conditions. This is a constitutive promoter from tobacco which is induced by heat and hormone shock, by wounding, and by biotic induction and infection. WO 94/21793 proposes to use this promoter for selecting crop protection agents or for protecting the plant from stress situations.

As a further example, EP 0 559 603 describes the constitutive promoter of cauliflower heat-shock protein hsp80. Parts of this promoter can also lead to constitutive expression in heterologous, non-constitutive promoters, for example in the case of inducible promoters, promoters which can be regulated by other means or inactivated promoters. EP 0 559 603 furthermore describes that genes which mediate resistance to insects, herbicide resistance genes, antimicrobial genes, antifungal genes, antiviral genes and anti-feedant genes can be under the control of this promoter. The hsp80 promoter has a very high constitute activity which, however, is only slightly elevated under stress conditions, which is a disadvantage.

The V-type $H^+$-ATPase (V-ATPase) plays a central role in the cells of higher plants since it contributes substantially to establishing the electrochemical $H^+$ gradient on the tonoplast. It accounts for a large proportion (7–35%) of the overall tonoplast protein (Klink et al. (1990) Bot. Acta 103, 24–31; Fischer-Schliebs et al. (1997) Biol. Chem. 378, 1131–1139). Moreover, V-ATPase is also found in the membranes of the Golgi vesicles. Thus, it is also relatively strongly expressed in cells which do not contain a large central vacuole. Plant V-ATPases are composed of at least 10 different subunits which, in defined stoichiometry, form a hollow enzyme of approx. 500 000 kD. In addition to the vacuole pyrophosphatase (V-$PP_i$ase), which is frequently expressed on the same endomembranes, V-ATPase plays a central role in processes such as cell division, cell elongation and metabolite or salt accumulation in the vacuoles.

Studies on the expression control of a plurality of V-ATPase genes in various plants (sugar beet, tobacco, carrot, maize, *Mesembryanthemum crystallinum*) have demonstrated that at least some V-ATPase genes show a coordinated expression with regard to the transcript quantities (Rausch et al. (1996) J. Plant Physiol. 148: 425–433; Löw et al. (1996) Plant Physiol. 110: 259–265; Löw and Rausch (1996) J. Exp. Bot. 47: 1725–1732; Kirsch et al. (1996) Plant Mol. Biol. 32: 543–547; Lehr et al. (1999) Plant Mol. Biol. 39: 463–475).

It is an object of the present invention to provide novel DNA constructs with plant constitutive promoters which show improved properties over the prior-art plant or viral promoters and which allow a strong, constitutive gene expression in all plant organs which is modulated by salt stress and other biotic or abiotic factors. In particular, the DNA constructs are intended to be suitable for expressing selection markers and resistance genes.

We have found that this object is achieved by a DNA construct in which a plant V-ATPase promoter or its functional equivalent operatively linked to a heterologous gene is present. According to the invention, this plant V-ATPase promoter may also be a deleted or hybrid V-ATPase promoter which remains functionally active as promoter.

Figure 1:
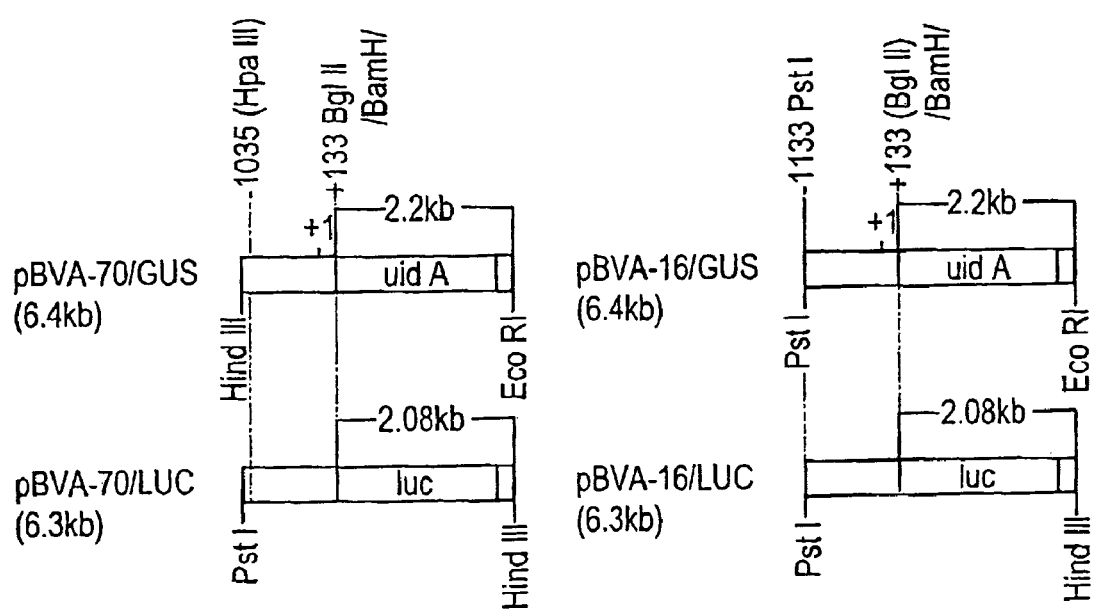
FIG. 1 is a schematic representation of the construct pBVA-70(16)/GUS and pBVA-70(16)/LUC.

The plant V-ATPase promoter may be derived from either dicotyledonous or monocotyledonous plants, for example from sugar beet, tobacco, barley, rice, potatoes, sunflowers, soya, tomatoes, Canola, wheat, oilseed rape, sorghum, carrots, maize, *Mesembranthemum crystallinum* or *Arabidopsis thaliana*.

The plant V-ATPase promoter is preferably the promoter of the *B. vulgaris* V-ATPase subunit A [SEQ ID No. 3], *B. vulgaris* V-ATPase subunit c isoform 1 [SEQ ID No. 2] or *B. vulgaris* V-ATPase subunit c isoform 2 [SEQ ID No. 1].

It is a further object of the invention to provide a novel constitutive plant promoter of the abovementioned type.

We have achieved this object by a polynucleotide encompassing the sequence of the promoter of *B. vulgaris* V-ATPase subunit c isoform 2 [SEQ ID No. 1] or a polynucleotide encompassing its functional equivalent.

Expedient embodiments of the invention are characterized in the subclaims.

Thus, the DNA construct according to the invention can encompass a second promoter which can be regulated in a different manner than the first promoter, thus allowing a more flexible expression control. Moreover, at least one further pyrimidine stretch can be inserted in the promoter, and this affects promoter activity.

The DNA construct according to the invention is preferably an expression cassette. It is further preferred that the heterologously expressed gene is a selection marker or a resistance-mediating gene. Examples of such heterologous genes are insecticidal toxins (such as, for example, of *Bacillus thuringiensis*), herbicide resistance genes, antimicrobial genes, antifungal genes, antiviral genes and antifeedant genes. Other suitable genes are, for example, selectable genes, reporter genes or killer genes. Examples of selectable genes are genes for resistance to antibiotics such as neomycin transferase genes, hygromycin phosphotransferase genes or phosphinothricin acetyltransferase genes or, alternatively herbicide resistance genes such as glufosinate, bromoxynil, sulfonamide or glyphosate resistance genes (for more information, see Glick and Thompson, Methods in Plant Molecular Biology and Biotechnology, CRC Press London, Chapter 6.7, pages 71–119). Examples of reporter genes are genes which code for chloramphenicol acetyltransferase (CAT), β-glucuronidase (GUS), luciferase (LUC), green fluorescent protein (GFP) or thaumatin. Examples of killer genes are the barnase gene, the TA29 gene or the Diphtheria toxin gene (for more information, see "Transgenic Plants", E. Gaulun and A. Breiman, Imperial College Press, London, 1997).

The invention furthermore provides a recombinant vector with a DNA construct according to the invention. This vector may also be a shuttle vector, which facilitates its handling.

In a further embodiment of the invention, the recombinant vector is an expression vector. Also, transformed microorganisms are provided together with the recombinant vector, for example a transformed *Agrobacterium tumefaciens*.

A preferred embodiment of the invention relates to a transgenic plant cell or a protoplast whose genome encompasses a DNA construct according to the invention.

This transgenic plant cell or protoplast can be derived both from a monocotyledenous and from a dicotyledenous plant. Preferred cells or protoplasts are those from sugar beet, tobacco, barley, rice, potatoes, sunflowers, soya, tomatoes, Canola, wheat, oilseed rape, sorghum, carrots, maize, *Mesembranthemum crystallinum* or *Arabidopsis thaliana*.

Especially preferred is a transgenic plant according to the invention whose genome encompasses a DNA construct according to the invention. The transgenic plant can be both a monocotyledenous and a dicotyledenous plant.

Especially preferred are plants such as sugar beet, tobacco, barley, rice, potatoes, sunflowers, soya, tomatoes, Canola, wheat, oilseed rape, sorghum, carrots, maize, *Mesembranthemum crystallinum* or *Arabidopsis thaliana*.

The invention furthermore provides a process for the controlled expression of a heterologous gene in a plant cell or a protoplast which allows a strong, constitutive gene expression in all plant organs which is modulated by salt stress and other biotic or abiotic factors. The process according to the invention comprises firstly transforming the cell or the protoplast with a DNA construct according to the invention, for example an expression cassette, and subsequently exposing the transformed cell or the protoplast to such a biotic or abiotic stress that the expression of the heterologous gene transformed by means of the DNA construct is controlled efficiently. This stress may occur in the form of salt stress, for example by NaCl or KCl, phosphate deficiency, nitrogen deficiency, sucrose deficiency, wounding, infection, temperature, drought, herbicides or mechanical stress. According to the invention, the plant cells or protoplasts used for the process can be obtained from a monocotyledenous or dicotyledenous plant, preferably from sugar beet, tobacco, barley, rice, potatoes, sunflowers, soya, tomatoes, Canola, wheat, oilseed rape, sorghum, carrots, maize, *Mesembranthemum crystallinum* or *Arabidopsis thaliana*.

The method according to the invention may also be used for the controlled expression of a heterologous gene in a plant. This method comprises regenerating cells or protoplasts transformed with a DNA construct according to the invention to give rise to a transgenic plant and subsequently exposing the transgenic plant to such a biotic or abiotic stress that the expression of the heterologous gene transformed by means of the DNA construct is controlled efficiently. This stress may occur in the form of salt stress, for example by NaCl or KCl, phosphate deficiency, nitrogen deficiency, sucrose deficiency, wounding, infection, temperature, drought, herbicides or mechanical stress. The transgenic plants used for the process can be obtained from a monocotyledenous or dicotyledenous plant, preferably from sugar beet, tobacco, barley, rice, potatoes, sunflowers, soya, tomatoes, Canola, wheat, oilseed rape, sorghum, carrots, maize, *Mesembranthemum crystallinum* or *Arabidopsis thaliana*.

Furthermore, the invention provides a method which allows the efficient production of a recombinant protein in a plant cell or a protoplast. To do this, the cell or the protoplast is transformed with a DNA construct according to the invention, and the transformed cell or the protoplast transformed thus subsequently exposed to such a biotic or abiotic stress that the recombinant protein transformed by means of the DNA construct is expressed. This stress may occur in the form of salt stress, for example by NaCl or KCl, phosphate deficiency, nitrogen deficiency, sucrose deficiency, wounding, infection, temperature, drought, herbicides or mechanical stress. The protein produced in this way can subsequently be isolated from the plant cell or the protoplast by methods known to those skilled in the art. The plant cells or protoplasts used for the process may be derived from a monocotyledenous or dicotyledenous plant. Especially preferred plant cells or protoplasts are those from sugar beet, tobacco, barley, rice, potatoes, sunflowers, soya, tomatoes, Canola, wheat, oilseed rape, sorghum, carrots, maize, *Mesembranthemum crystallinum* or *Arabidopsis thaliana*.

Moreover, the invention provides a method which allows the efficient production of a recombinant protein in a plant. The method comprises regenerating cells or protoplasts which have been transformed with a DNA-construct according to the invention to give rise to a transgenic plant and subsequently exposing the resulting transgenic plant to such a biotic or abiotic stress that the recombinant protein transformed by means of the DNA construct is expressed. This stress may occur in the form of salt stress, for example by NaCl or KCl, phosphate deficiency, nitrogen deficiency, sucrose deficiency, wounding, infection, temperature, drought, herbicides or mechanical stress. The protein produced in this way can subsequently be isolated from the plant. The plants used for the process may be monocotyledenous or dicotyledenous plants. Especially preferred are plants such as sugar beet, tobacco, barley, rice, potatoes, sunflowers, soya, tomatoes, Canola, wheat, oilseed rape, sorghum, carrots, maize, *Mesembranthemum crystallinum* or *Arabidopsis thaliana*.

Moreover, the present invention extends to the use of a DNA construct according to the invention for producing a recombinant protein in a plant, plant cell or a protoplast. The invention also extends to recombinant proteins produced by one of the methods according to the invention.

However, the DNA construct according to the invention may also be used for expressing a gene in a plant under biotic or abiotic stress. Moreover, the plant V-ATPase promoter according to the invention can be used for expressing a gene in a plant under biotic or abiotic stress. This promoter may also be used in the form of a deleted or hybrid V-ATPase promoter. Plant V-ATPase promoters according to the invention from dicotyledenous or monocotyledenous plants may be used. The use of plant V-ATPase promoters from sugar beet, tobacco, barley, rice, potatoes, sunflowers, soya, tomatoes, Canola, wheat, oilseed rape, sorghum, carrots, maize, *Mesembranthemum crystallinum* or *Arabidopsis thaliana* is preferred. Especially preferred are the V-ATPase promoters of the *Beta vulgaris* V-ATPase subunit A [SEQ ID No. 3], *B. vulgaris* V-ATPase subunit c isoform 1 [SEQ ID No. 2] or *B. vulgaris* V-ATPase subunit c isoform 2 [SEQ ID No. 1]. Moreover, at least one additional pyrimidine stretch may be inserted into the promoter used.

The invention furthermore relates to a plant cell or protoplast which has been transformed with a DNA construct according to the invention and which is resistant to biotic or abiotic stress. This stress may occur in the form of salt stress, for example by NaCl or KCl, phosphate deficiency, nitrogen deficiency, sucrose deficiency, wounding, infection, temperature, drought, herbicides or mechanical stress. A transformed salt-stress-resistant plant cell or protoplast is preferred.

The invention furthermore extends to a plant transformed with a DNA construct according to the invention which is resistant to biotic or abiotic stress, preferably a transformed salt-stress-resistant plant.

A total of three different V-ATPase genes were isolated from a genomic library of *Beta vulgaris*. The cDNA clones and the genomic clones for the subunits A and c1, which correspond to the peripheral V1 complex and the membrane-integrated V0 complex, have already been described (Lehr et al., Plant Molecular Biology 39, 463–475 (1999, GenBank/EMBL-Datenbank: X98767, X98851, Y11038, Y11037).

RNA blot analyses with gene-specific cDNA probes show expression of the cloned subunits A and c1 and of the isoforms c2, which have been cloned for the purposes of the present invention, in roots, leaves and in a sugar beet suspension culture.

Surprisingly, it has emerged that all three promoters show a very high activity, which, as a rule, exceeds that of the 35S CaMV promoter.

It seems that polypyrmidine sequences which are present in the promoters play an important role in this context. The isoforms A and c1 each have two such sequence stretches while the isoform c2 only has one such sequence stretch.

It has now surprisingly been found within the context of the present invention that the plant V-ATPase promoters are outstandingly suitable for constructing DNA constructs which can preferably be used as plant expression cassettes.

These expression cassettes can be used for causing, in the plant, an expression of heterologous proteins which is governed by environmental effects. The invention thus allows the plant or the plant cell to be equipped with one or even more heterologous genes which are induced in the plant additionally to its constitutive expression "when required" by the plant (when the environment changes).

Luciferase reporter gene studies on the promoter V-ATPase A and c1 from sugar beet and the 35S promoter were carried out on sugar beet cell cultures under salt stress (Lehr et al., Plant Mol. Biol. 39, 463–475, 1999). An induction of the promoter activity was detected for the isoforms A and c1. The 35S CaMV promoter activity, which was studied for comparison reasons, is not induced by salt and indeed repressed. Within the invention, a surprising induction of all three promoters by 100 mM NaCl or 100 mM KCl was found, even though all three promoters differ with regard to their DNA sequence.

Surprisingly, it has furthermore been found that the promoters according to the invention show no reduced promoter activity in the case of phosphate deficiency/nutrient deficiency, which is in contrast to the 35S CaMV promoter. Thus, the constitutive expression remains ideally stable.

In contrast, the promoter activity is induced by wounding, while the 35S CaMV promoter is not induced under comparable conditions. Also, it has been found that the promoter activity is affected by sucrose deficiency; it reduces the activity of c1, but not the activity of the 35S CaMV promoter.

It has also been found that the promoter activities are affected by abiotic factors such as high (30–35° C.) or low (2–5° C.) temperatures.

In addition, it has been found that various deletions can be introduced into this promoter, which leads to this promoter showing either a) an increased activity, b) an essentially identical activity to that of the native promoter, c) a reduced activity, d) a higher inducibility under stress conditions than the native promoter, or e) a lower inducibility under stress conditions than the native promoter.

"Operatively linked" means such an arrangement that the normal function of the components can be carried out. An encoding sequence which is "operatively linked" with a control sequence therefore indicates a configuration in which the encoding sequence can be expressed under the control of the sequences.

The term "control sequences" describes DNA sequences which are required for expressing an operatively linked encoding sequence in a host organism. The control sequences which are suitable for, for example, prokaryotes, encompass a promoter, an optional operator sequence, a ribosome binding site and, possibly, other sequences which are not well understood as yet. Eukaryotic cells are known for containing promoters, polyadenylation signals and enhancers.

The term "gene" refers to a DNA sequence which encodes a bioactive polypeptide which can be isolated, or a precursor. The polypeptide can be encoded by a full-length sequence or by any part of the encoding sequence as long as the enzymatic activity is retained.

An aspect of the invention is therefore a DNA construct with a plant V-ATPase promoter or its functional equivalent, operatively linked with a heterologous gene. It is known that minor changes may be present in the promoter sequence, for example caused by the degeneration of the genetic code, without substantially affecting its activity. The present invention therefore also relates to "functional equivalents" of the plant V-ATPase promoters which are operatively linked with a heterologous gene.

The term "functional equivalents" characterizes all DNA sequences which are complementary to a DNA sequence, which hybridize with the reference sequence under stringent conditions and which show an activity which is similar to that of a plant V-ATPase promoter.

"Stringent hybridization conditions" are to be understood as meaning those conditions under which hybridization takes place, and remains stable, at 60° C. in 2.5×SSC buffer followed by repeated washing steps at 37° C. at a lower buffer concentration.

"Heterologous genes" are DNA sequences which encode peptides or proteins which are other than the plant V-ATPase subunits A, c1 or c2.

A "deleted or hybrid V-ATPase promoter" is any V-ATPase promoter which has a deletion or whose make-up is altered and which still has promoter activity.

The invention will be described in greater detail hereinbelow in connection with the drawings.

I. Method of Obtaining the Genomic Library of *Beta vulgaris* L.

Generation of a Genomic Library

A genomic library was established with leaf material of *Beta vulgaris* L. type 3A39111 in the "Lambda Fix II/Xho I partial fill-in" vector by Stratagene.

The use of the "Lambda Fix II/Xho I partial fill-in kit" allows genomic DNA fragments to be cloned efficiently without the laborious size fractionation via an agarose gel. To this end, the genomic DNA is subjected to a partial digest with the restriction endonuclease Sau3 AI, and the free ends are filled up with Klenow polymerase, incorporating dGTP and dATP. The resulting 3'-AG-5' overhangs prevent autoligation of the genomic DNA fragments. Also, the 3'-CT-5' overhangs of the vector (vector digested with Xho I, partially filled-in ends with dCTP, dTTP) prevent a religation of the central vector fragments ("stuffer element"). Amplification of wild-type Lambda Fix II phages (containing the stuffer element) is also prevented by using the P2 lysogenic *E. coli* strain XLI-Blue MRA(P2). Thus, the method used allows recombinant genomic clones in the desired size range to be obtained in very high yield.

Partial Digest of Genomic DNA

The optimal enzyme concentration for obtaining fragments in the required size range of 15–23 kb is determined by a test digest. To do this, individual reactions together with a DNA marker are fractionated in a low-concentration agarose gel, and the average fragment sizes are determined. Since the electrophoretic fractionation causes a delay in the migration behavior in particular in the high-molecular DNA range, fragment size cannot be determined directly via the maximum fluorescence intensity. Rather, Seed et al. (1982) maintain that fragment size is overestimated by a factor of 2. To obtain fragments in the desired size range, only half of the optimal enzyme concentration determined via gel electrophoresis is therefore employed for the preparative digest.

Test Digest

For the test digest, the restriction enzyme Sau3A I (10 U/µl, Promega) is diluted in restriction buffer [1× buffer B (Promega) supplemented with 0.1 mg/ml acetylated BSA (Sigma)] to concentrations of 0.1 U/µl, 0.05 U/µl, 0.025 U/µl, 0.01 U/µl], and the enzyme solutions are stored on ice. 25 µg of $CsCl_2$-purified genomic DNA dissolved in TE buffer are resuspended in a total volume of 1.125 ml of restriction buffer (see above) and stored in reaction vessels on ice in 225 µl-aliquots. The DNA solutions (in each case 5 pg of DNA) are preheated for approximately 20 minutes in a waterbath at 37° C., and the individual reactions are started by adding 25 µl of the restriction enzyme solution. 25 µl of pure buffer solution are added to a control sample. The digest is carried out for 2 minutes at 37° C. and is stopped by adding 10 μl-portions of 0.5 M Na$_2$ EDTA. The DNA is then precipitated by adding 1 volume of isopropanol and 0.1 volume of 3 M sodium acetate (pH 7), washed with 70% ethanol, dried, and then resuspended in 10 μl-portions of TE buffer. The reaction batches are separated by electrophoresis overnight in an 0.5% TAE gel (track length 19 cm) stained with ethidium bromide, overnight at 2 V/cm and RT. The size marker used in the present experiment was lambda DNA digested with Hind III, and the 1-kb-DNA ladder (Gibco, BRL).

Preparative Digest

The conditions for the preparative digest correspond essentially to those of the test batch. To standardize the reactions, DNA concentration, overall volume of the reaction batch, and time, remain unchanged. The enzyme concentration results from the test digest. 100 μg of genomic DNA is digested in aliquots (see above), 0.11 volume of 10×STE and 0.3 volume of 1×STE are added, and the mixtures are then extracted twice using 1 volume of phenol/chloroform/isoamyl alcohol (25:24:11, v/v/v). Precipitation takes place after addition of 0.5 volume of 7.5 M sodium acetate, 2 volumes of absolute ethanol, 30 minutes at −20° C. The DNA is washed with 70% ethanol, dried at room temperature, and resuspended in 200 μl of TE buffer while the pellets are combined. All centrifugation steps are carried out for 10 minutes at 12,000 g and 4° C. The digest is stored at −20° C.

10×STE: 0.1 M NaCl, 10 mM Tris-HCl, pH 8, 1 mM Na$_2$ EDTA

Klenow Reaction

50 μg of the partially digested genomic DNA in an overall volume of 350 μl of 1× fill-in buffer (1× Klenow buffer: 50 mM Tris-HCl, pH 7.2, 10 mM MgSO$_4$, 0.1 mM DTT, Promega; 0.166 mM dGTP, 0.166 mM dATP) with 15 U Klenow polymerase (5 U/μl, Stratagene). The reaction is stopped by adding 0.5 volume of STE buffer (0.1 M NaCl, 10 mM Tris-HCl, pH 8, 1 mM Na$_2$ EDTA, pH 8), and the DNA is then treated with phenol and chloroform. After 0.5 volume of sodium acetate and 2 volumes of absolute ethanol have been added, the DNA is precipitated for 30 minutes at −70° C., pelleted for 15 minutes at 12,000 g and 4° C. and washed in 70% ethanol. The dried pellet is resuspended in TE buffer and stored at −20° C.

Ligation into the Lambda Fix II/Xho I Partial Fill-In Vector

In a reaction volume of 10 μl, 1 μg of lambda DNA (1 μg/μl Lambda Fix II/Xho I partial fill-in vector) and 0.4 μg of genomic DNA fragments in ligase buffer (10 mM Tris-HCl, pH 7.8, 10 mM MgCl$_2$, 10 mM DTT, 1 mM rATP, Promega) are resuspended on ice and incubated overnight at 6–8° C. with addition of 3.75 U of T4 DNA ligase (15 U/μl, Promega). To check the ligation efficacy, 0.3 μg of the test insert (50 ng/μl, 12-kb pMF test insert; BamH I fragment partially filled up with dATP, dGTP) is ligated with 1 μg of lambda DNA under the abovementioned conditions as a control batch. The DNA is packaged the following day.

Packaging of the Lambda DNA

To generate a representative genomic library, the total number of independent clones required is calculated using the formula described by Clarke and Carbon (1976). Aliquots of the ligation reaction are packaged, the titer is determined, and this result is used for calculating the number of independent clones per packaging reaction. If required, further packaging reactions are carried out. In total, the calculated minimum number of independent clones should be reached. The Gigapack III Gold packaging extract by Stratagene was used to package the ligation products. A packaging extract (50 μl) is partially defrosted by holding it in the hand, 1 μl of ligation batch are added, and the mixture is stored on ice. To check the packaging efficacy, 0.2 μg of lambda control DNA (wild type c1857 Sam7, 0.2 μg/μl) are packaged in the same manner. The extract is carefully resuspended using a pipette and then incubated for 2 hours at room temperature. The reaction is stopped by adding 500 μl of SM buffer (0.01% gelatin, 50 mM Tris-HCl, pH 7.5, 100 mM NaCl, 8 mM MgSO$_4$) and 20 μl of chloroform, and the solution is mixed by careful shaking. The mixture is then centrifuged for 1 minute at 16,000 g and 4° C. The supernatant is transferred into a reaction vessel and stored at 4° C. until use. The titer plates are established the same day.

The following dilution levels of the individual packaging extracts are used:

| Packaging extract | Dilution level |
| --- | --- |
| Ligation of *B. vulgaris* genomic DNA | $1 \times 10^0 / 1 \times 10^{-1}$ |
| Ligation of the control insert (pMF) | $1 \times 10^{-1} / 1 \times 10^{-2}$ |
| Control DNA (wild type c1857 Sam7) | $1 \times 10^{-3} / 1 \times 10^{-4}$ |

Amplification of the Genomic Library

To recover a highly concentrated phage suspension which can be stored at −80° C. as a stable stock culture, the genomic library of *B. vulgaris* was amplified. The minimum number of independent clones required for the amplification should represent the entire genome (Clarke and Carbon, 1976).

Amplification takes place in the form of plate lysates (150 mm Ø LB agar plate). The amount of packaging extract required depends on the minimum number of independent clones (see above). 600 μl of competent host cells per plating batch are infected with 50,000 pfu each and incubated for 15 minutes at 37° C. with gentle shaking. 6 ml of top agar is used for plating. The incubation time is approximately 8 hours at 37° C. Plaque size should reach a diameter of 1–2 mm. The plates are then overlaid with 10 ml of SM buffer and incubated overnight in a refrigerated chamber on a tumble shaker at the lowest possible speed. The supernatants are transferred into a sealable centrifuge vessel, the plates are rinsed with 2 ml of SM buffer, and the supernatants are combined. After addition of chloroform (end concentration 5%), the phage suspension is incubated for 15 minutes at room temperature and separated from bacterial residues by centrifugation for 10 minutes at 2000 g. The supernatant is transferred into a sterile vessel, treated with chloroform (end concentration 3%), and can now be stored for several months at 4° C. After the titer of the amplified genomic library has been determined, aliquots are stored at −80° C. in 7% DMSO (dimethyl sulfoxide) to provide a stock solution. The following dilution levels are employed for the titer determination (90 mm Ø LB plates): $1 \times 10^{-6}$, $1 \times 10^{-7}$, $1 \times 10^{-8}$.

II. Methods for Cloning Promoter/Reporter Gene Constructs for the V-ATPase Promoters A, c1 and c2, with the Reporter Genes Luciferase (or β-Glucuronidase)

Subcloning Genomic Clones with Promoter Regions

A single type of genomic clones was obtained for subunit A, while two different isoforms were isolated for subunit c clones. To subject the clone of the genomic subunit A to sequence analysis, a 4.3 kb EcoRI fragment (pBVA/70)

which hybridizes with subunit A cDNA was subcloned into the vector pBluescript II SK+. For subunit c, an 8 kb XbaI/HindIII fragment (pBVA/16-1) and a 5 kb EcoRV/HindIII fragment were subcloned into the same vector.

Cloning of Promoter/Reporter Gene Constructs

BVA/70 Promoter

A 1.3 kb HpaII fragment of the pBVA/70 clone was made blunt-ended using Klenow polymerase and ligated into the SmaI site of the vector pBluescript in order to obtain pBVA/70. Restriction with HindIII and BglII resulted in a 1.3 kb promoter fragment with its 3' end in position −28 relative to the transcription start. To obtain the promoter-GUS fusion, the HindIII/BglII was ligated with the BamHI/EcoRI GUS cassette of pBI221 (Clontech) and then cloned into the vector pBluescript in order to obtain pBVA/70p-GUS. To obtain the promoter-LUC fusion, a PstI/BglII promoter fragment was ligated upstream of the BamHI/HindIII cassette of pCaMVLN and cloned into the vector pBluescript.

BVA/16-1 Promoter

The BamHI/EcoRI GUS cassette of plasmid pBI221 (Clontech) was cloned into pBluescript (pBGUS), from which it was excised using BamHI and SalI. A 1.3 kb PstI/BglII promoter fragment of pBVA/16-1 with its 3' end in position −40 relative to the transcription start was ligated with the GUS cassette and cloned into PstI/SalI-digested pBluescript in order to obtain pBVA/16-1p-GUS. The promoter-LUC fusion was cloned as described for BVA/70 (see above). The plasmids pFF19G and pCaMVLN were used in each case as standards for GUS and LUC.

Characterization of the Promoter/Reporter Gene Constructs

To compare the relative promoter activities of subunits A and c1 of the *Beta vulgaris* V-type $H^+$-ATPase, fragments of approximately 1.2 kb were isolated from the region upstream of the encoding region of the genomic clones pBVA-70 and pBVA-16/1. In this context, the term promoter characterizes the 5'-regulatory region and thus not only the promoter region, but also parts of the 5'-untranslated leader. These fragments were subsequently ligated into the phagemid vector pBluescript II SK+ upstream of the corresponding (see below) reporter gene cassettes. The reporter gene used was, in addition to β-glucuronidase structural gene from *Escherichia coli* (uid A), the *Photinus pyralis* luciferase gene (Jefferson, 1987; de Wet et al., 1987). The promoter/reporter gene constructs constitute "transcriptional fusions" since the 3' ends of the promoter fragments employed are in each case 30-4 bp upstream of the translation start of the genomic clones. FIG. 1 is a schematic representation of the individual constructs. The expression vectors are hereinbelow termed pBVA-70 (or 16)/GUS and pBVA-70 (or 16)/LUC.

Characterization of the pBVA-70 Promoter Fragment

The total size of this fragment is 1.237 kb. It encompasses the region between positions −1035 to +202 relative to the transcription start (+1) of the genomic clone pBVA-70, and thus contains, in addition to the promoter, most of the adjacent leader region (total length of leader=230 bp).

Characterization of the pBVA-16/1 Promoter Fragment

The total size of this fragment is 1.265 kb. It encompasses the region between positions −1130 to +135 relative to the transcription start (+1) of the genomic clone pBVA-16/1, and thus contains, in addition to the promoter sequence, most of the adjacent leader region (total length of leader=174 bp).

FIG. 1 is a schematic representation of the construct pBVA-70 (16)/GUS and pBVA-70 (16)/LUC. Fragments (approx. 1.25 kb) from the region of the 5'-untranslated region of the genomic clones pBVA-70 and pBVA-16/1 were ligated into the phagemid vector pBluescript II SK+ upstream of the respective reporter gene cassette. To prepare the promoter/GUS construct, the BamHI/EcoRI cassette of vector pBI-221 by Clontech was used. In addition to the β-glucuronidase structural gene from *E. coli*, it carries the polyadenylation region of the nopalin synthase gene (Ti plasmid, *Agrobacterium tumefaciens*). The promoter/LUC constructs were obtained using the BamHI/HindIII cassette of the vector pCaMVLN. It contains the *Photinus pyralis* luciferase structural gene and the polyadenylation region of the nopalin sythase gene. The figures characterize the position of the cleavage sites of the promoter fragments used relative to the transcription start (+1) of the genomic clones.

Generation of a BVA/16-2 Promoter/LUC Construct

A further reporter gene employed for preparing a construct was the *Photinus pyralis* luciferase gene (de Wet et al. 1987), EMBL Acc. No. M15077. To prepare a promoter/luciferase construct, the BamHI/HindIII cassette is excised from vector PCLN (pCaMVLN; Callis et al. 1987). It contains the *Photinus pyralis* luciferase structural gene (LUC) with the polyadenylation region of the nopalin synthase gene. This cassette is cloned into the vector pBluescript II SK (Stratagene) which has been cleaved with BamHI/HindIII. The promoter/leader fragment of the gene of subunit c (isoform 2) of the *Beta vulgaris* V-type $H^+$-ATPase is excised from the construct pBVA/16-2 GUS (see above) using BamHI. The vector pBluescript II SK, into which the luciferase cassette has been cloned, is also opened up using BamHI, and the promoter with sticky ends thus cloned upstream of the luciferase. The position of the promoter fragment in the construct in the correct orientation (5'→3') upstream of the luciferase gene is checked by a variety of restriction digests (for example BamHI, SalI or XmnI). The transitions from the MCS of the vector to the promoter and from the other side of the MCS to the luciferase are checked by sequencing with the vector primers "M13 Forward" and "M 13 Reverse". The promoter/leader LUC construct is termed pBVA/16-2 LUC.

III. Methods for Measuring the Promoter Activities in Beta Cell Cultures

Ballistic Transformation

The ballistic transformation method (particle gum bombardment) was employed for the transient expression of promoter gene constructs in *Beta vulgaris* cell suspension cultures. This is a direct gene transfer method, whereby the DNA reaches the plant cell owing to the fact that the cell wall is destroyed mechanically (Sanford et al. (1987)).

A Biolistic PDS-1000/He particle delivery system, BIO-RAD was used.

During the experiment, the gas pressure in the pressure chamber rises and leads to the bursting disks being destroyed. The number of bursting disks used governs the pressure generated in the pressure chamber. As a consequence, the stream of helium gas escapes in a shocklike manner from the pressure chamber into the previously generated vacuum chamber. The escaping stream of gas accelerates the particle-coated macrocarrier, which is slowed down after only a few centimeters by means of a retaining net. The DNA-loaded microcarriers (here: tungsten particles), in contrast, pass through the interstices of the net and rupture the cell walls when they hit the plant material.

Microcarrier Preparation

In a reaction vessel, 1 ml of 70% ethanol is added to 30 mg of tungsten particles (microcarrier), and the mixture is vortexed for 20 seconds. A subsequent incubation for 10 minutes allows the particles to settle, and they are then sedimented for 30 seconds at 1300 g (unbraked) at room temperature. After the supernatant has been removed, the particles are washed with 500 ml of sterile double-distilled $H_2O$ as follows: vortex for 10 seconds, leave to stand for 10 minutes, unbraked centrifugation for 30 seconds at 1300 g. The sedimented particles are then treated with 500 µl of 50% glycerol and mixed by vortexing. They are stored at −20° C.

Loading of the Microcarriers with DNA

The plasmid DNA required for the transformation should be free from impurities (protein, RNA) and should predominantly be present in supercoiled form. To isolate the DNA, commercially available plasmid kits are employed. To load the particles (microcarriers), it is recommended to assume a minimum number of 10–15 bombardments. The microcarriers rapidly settle out in the suspension during preparation, and small volumes make resuspending difficult. The volumes which follow are in each case per bombardment.

All steps with the exception of the centrifugation steps are carried out in a clean bench. The particle suspension is mixed thoroughly on a Vortex mixer, and 9-µl-batches of the solution are subsequently transferred into a reaction vessel. 1 µl of plasmid DNA (1 µg/µl in TE buffer) is added with constant vortexing. The mixture is stored for 15 minutes in an ice bath. Then, 9 µl of 2.5 M of $CaCl_2$ (sterile), 3.6 µl of 1.2 mM spermidine (filter-sterilized) and 18.2 µl of absolute ethanol are subsequently added in succession, with gentle vortexing. After incubation for 10 minutes in an ice bath, the particles are sedimented for 5 seconds at 180 g at room temperature, and the supernatant is then removed. 6.4 µl of absolute ethanol are added, and the particles are carefully resuspended by "finger vortexing" and stored in the ice bath until further use.

Preparation of the Cell Material

For the gene transfer, the cell suspension culture used (here: 3–4 day-old *Beta vulgaris* culture) is transferred to agar plates. To improve transformation efficiency, the osmotic value of the medium is increased by adding mannitol and sorbitol, and the cells are preincubated on this medium for approx. 4 hours. The effect of the osmotic treatment on the transformation efficiency of the plant cells can probably be attributed to the fact that plasmolysis occurs (Vain et al., 1993). It is possible that this prevents the cytoplasm from leaking out after the particle has entered the cell (Armaleo et al., 1990; Sanford et al., 1992).

All steps, with the exception of the centrifuging steps, are carried out in the clean bench. To this end, 10 ml-disposable pipettes, tweezers, filter paper disks (45 mm Ø), Büchner funnels and a wash flask are prepared. The materials with the exception of the disposable pipettes and the tweezers are autoclaved beforehand. Petri dishes (50 mm Ø) provided with Gamborg B5 medium (0.9% agar supplemented with 0.5 g/l casein hydrolysate, 125 mM sorbitol, 125 mM mannitol, after Ingersoll et al. 1996) are also used.

The Büchner funnel is provided with a filter paper disk. Then, 3.3 ml of suspension culture, corresponding to approx. 1 ml of cell packed volume (see below) are distributed uniformly on the filter surface using a disposable pipette. The excess medium is removed via the wash flask by briefly applying a vacuum (approx. 2 seconds). The filter is transferred to a Petri dish containing nutrient medium, and the cells prepared in this way are stored in the clean bench at room temperature for 3–4 hours until the gene transfer takes place.

CPV Determination

At the beginning of the experiment, the cell packed volume (CPV) of the cell suspension culture is determined. To this end, 10 ml of the suspension are removed under sterile conditions and sedimented for 5 minutes at 1130 g (swing-bucket rotor) in a 15 ml graduated centrifuge tube. The cell packed volume is determined with reference to the graduation.

Transformation

All steps with the exception of the ultrasonic treatment of the particle suspension (see below) are carried out in the clean bench. Beforehand, the inside of the particle gun and all metal and plastic supports are cleaned with absolute ethanol. Equally, the retaining nets and the bursting disks are treated with ethanol and dried in the clean bench. The macrocarriers (M-20, BIORAD) are sterilized by briefly immersing them in absolute ethanol and transferring them into a desiccator.

The tungsten particle suspension is sonicated for 2 seconds at the maximum setting (Sonopuls HD 60, Bandelin), and 5-µl-portions of the suspension (approx. 422 µg particles, 0.78 µg DNA) are carefully pipetted onto the macrocarrier surface. To prevent settling out, the particles are kept in solution between the pipetting steps by repeatedly finger-vortexing the reaction vessel. Then, a vacuum is applied to the desiccator for 20 minutes. Before the bombardment, the bursting disks (3 disks), the particle-loaded macrocarriers and the retaining net are fixed in accordance with the instructions. Position 3 is chosen for the Petri dish support charged with the suspension culture. Then, the chamber is evacuated down to a vacuum of 27 inches (Hg), and the helium gas is passed into the pressure chamber. At a pressure of 1200 psi, the bursting disks rupture. The Petri dishes are then sealed under sterile conditions (Parafilm), and the cultures are incubated for 2 days at 24° C. in permanent darkness.

Histochemical Detection of β-Glucuronidase Activity

The transient expression of the β-glucuronidase structural gene can be detected by a histochemical method. To this end, after transformation has been carried out and an incubation time of 24 hours has elapsed, paper filters of suspension cultures are transferred into a Petri dish (50 mm Ø) and overlaid with 1 ml of reaction buffer (see below). Incubation is carried out overnight at 37° C. in an incubator. The number of zones which are stained blue is determined at 40× magnification using a stereomicroscope.

To prepare the reaction buffer, 70 mg of X-Gluc (5-bromo-4-chloro-3-indolyl-β-D-glucuronic acid, Duchefa) are predissolved in 500 µl of dimethyl sulfoxide and the solution is resuspended in 100 ml of a buffer solution (115 mM $NaH_2PO_4 \times 2H_2O/Na_2HPO_4 \times 2H_2O$ pH 7, 10 mM $Na_2$-EDTA, 0.5 mM $K_3$ [Fe(CN)$_6$], 0.5 mM $K_4$ [Fe(CN)$_6$]). Aliquots of the reaction buffer thus obtained can be stored over several weeks at −20° C.

Methods for Quantifying the β-Glucuronidase and Luciferase Activities

To quantify the enzyme activity of the reporter gene products used, detection methods were used which rely on bioluminescence and chemiluminescence. To determine the enzyme activity, the proteins are extracted beforehand. The "light quantity" generated in the subsequent enzymatic reactions is quantified in a luminescence spectrometer (Berthold, Lumat 9501). The measurement value obtained represents the light quantity integrated over a period of time. The measurement value is indicated as light units measured, "LU".

Preparation of the Protein Extracts

The proteins are extracted using the "GUS-Light Assay" (Tropix) and the "Luciferase Assay System" (Promega). To prepare the protein extracts, the suspension cultures are removed from the paper filters using a spatula, the fresh weight is determined, and the cells are then disrupted using a pestle and mortar with addition of liquid nitrogen. Extraction buffer (500 µl/g FW) is pipetted to the frozen material, and the extract is defrosted and then thoroughly homogenized. Using cut-off pipette tips, the suspension is transferred into a reaction vessel on ice and centrifuged for 1 minute at 4° C. and 16,000 g. The supernatants are kept on ice until the activity is determined.

Extraction Buffer: ("GUS-Light Assay")

The buffer solution (GUS lysis solution) is supplemented with β-mercaptoethanol prior to use (final concentration: 50 mM sodium phosphate buffer pH 7, 10 mM Na$_2$-EDTA, 0.1% SDS, 0.1% Triton, 10 mM β-mercaptoethanol). The solution is stored at room temperature until use.

Extraction Buffer: (Luciferase Assay System)

The buffer (cell culture lysis reagent), which has a concentration of 5×, is diluted with sterile double-distilled H$_2$O at a ratio of 1:5 (final concentration: 25 mM Tris-HCl pH 7.8 with H$_3$PO$_4$, 2 mM CDTA, 2 mM DTT, 10% glycerol, 1% Triton) and stored at room temperature until use.

Determination of β-Glucuronidase Activity

Detection reaction:

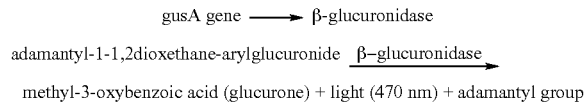

To detect the β-glucuronidase activity, the GUS-Light Kit (Tropix) was used. The manufacturer's instructions were followed for this.

Protein extract, reaction buffer and "accelerator" are prewarmed to room temperature prior to use. After 20 µl of protein extract have been transferred into a test tube (10 ml), the reactions are started by the staggered (20 seconds) addition of reaction buffer (in each case 180 µl). The batches are incubated for 1 hour at room temperature in permanent darkness. Then, in each case 300 µl of accelerator solution are pipetted to the reactions (staggered, see above). Immediately after the solution has been added, the individual samples are measured in a luminescence spectrometer (Lumat 9501, Berthold) with a delay of 5 seconds over a period of, again, 5 seconds.

Negative Control

The absolute values determined by the luminescence spectrometer cannot be attributed directly to the activity of a foreign gene. To determine the background value, which, in the case of β-glucuronidase, may possibly also be attributed to a comparable, endogenous activity, untransformed cell suspension cultures are studied by means of the above-described detection methods. The measurement values of this negative control (BW, blank value; see Tables 1a and 1b) additionally also contain the background values caused by buffer substances. To calculate the promoter activities, the blank value is subtracted from the measurement values of the transformed culture.

Reaction Buffer ("GUS Reaction Buffer")

Prior to use, the substrate (glucurone, chemiluminescent substrate) is diluted 1:100 in "GUS Reaction Buffer" (not complemented: 0.1 M sodium phosphate buffer, pH 7, 10 mM Na$_2$-EDTA).

Luciferase Activity Determination

Detection reaction:

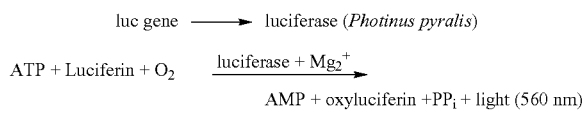

To determine the luciferase activity, the Luciferase Assay System (Promega) was used. The ratio of protein extract to reaction buffer was varied.

Both protein extract and reaction buffer (see below) are prewarmed to room temperature. After in each case 20 µl (100 µl) of protein extract have been transferred into a 10 ml test tube, 100 µl (50 µl) of reaction buffer are added to the sample and the batch is then measured immediately in the luminescence spectrometer (Lumat 9501, Berthold) over a period of 10 seconds. According to what has been said for determining the β-glucuronidase activity, a blank value is determined which is used for correcting the measurement values of transformed cultures.

Reaction Buffer ("Luciferase Assay Reagent")

To prepare the reaction buffer, the substrate (Luciferase Assay Substrate) is dissolved in the "Luciferase Assay Buffer" (final concentration: 470 µM luciferin, 270 µM coenzyme A (lithium salt), 530 µM ATP, 20 mM trizin, 1.07 mM (MgCO$_3$)4Mg(OH)2×5H$_2$O, 2.67 mM MgSO$_4$, 0.1 mM Na$_2$-EDTA, 33.3 mM DTT, pH 7.8). The reaction buffer is divided into aliquots and stored at −70° C.

Determination of the Relative Promoter Activity

To quantify the promoter activity in promoter/reporter gene constructs, the transient expression of the reporter genes is measured by means of the above-described enzymatic detection methods. However, when using direct gene transfer to determine promoter activity, the variation, between the individual transformations, of the measurement values obtained is frequently substantial. In the case of ballistic transformation, the efficiency of the gene transfer is affected on the one hand by the physiological state of the transformed tissue after the treatment. On the other hand, physical factors are also of importance, for example differences in the loading of the microcarriers or in the distribution of the particle suspension on the macrocarrier. The measurement values must therefore be supported by a calibration of the measurement system.

Theory of Calibration

Test Plasmid

Test promoter: To quantify the promoter activity, the transient expression of the reporter gene is determined by determining the enzymatic activity of its gene product. However, the promoter activity of the test promoter cannot be shown as an absolute value of the enzymatic activity determination. Quantification requires a comparison with the constitutive promoter (standard promoter).

Standard promoter: In a parallel set-up, the expression of the reporter gene under a constitute promoter (here: CaMV 35S promoter) is studied. The promoter activity of the test promoter is indicated as the ratio activity$_{test\ promoter}$/activity$_{standard\ promoter}$, the activity of the standard promoter equalling 1. Using expression of the reporter gene under a standard promoter as the reference base allows, inter alia, a comparison of the results from repeated experiments.

Calibration Plasmid (Internal Standard)

To record the transformation efficiency of individual bombardments (transformations), the microcarriers are loaded simultaneously with a test plasmid and a calibration plasmid. The constructs used (test plasmid, calibration plasmid) carry different reporter genes, thus allowing their expression data (enzyme activities) to be recorded in parallel.

The structural gene of the calibration plasmid is under the control of a constitutive promoter (here: CaMV d35S, strength 35S promoter). The measurement values (enzyme activities) for the calibration plasmid reflect the transformation efficiencies of individual bombardments. All measurement values obtained for the internal standard (calibration plasmid) in one experiment are considered together and divided by the maximum value obtained in the experiment. Thus, the highest measurement value leads to a transformation efficiency of 1 (corresponds to 100%). The transformation efficiency (from 0–1) is indicated as relative light units "rLU". The absolute measurement values obtained in the study for the test plasmid (test promoter, standard promoter) are corrected taking into consideration the transformation efficiency of the bombardment. To this end, the activity determined for the test plasmid is divided by the transformation efficiency. The corrected values are termed relative activities. The ratio of test plasmid to calibration plasmid (7:3, w/w) is retained in all experiments.

Copy Number

Identical quantities of test plasmid DNA are employed in the transformation (here approx. 0.7 μg per bombardment). When comparing the activities of test promoters and standard promoter (see above), plasmid size, i.e. the number of molecules (copy factor) per pg of test plasmid DNA must be taken into consideration. The number of standard promoter molecules (test plasmid) employed per bombardment is taken as the reference value and made equal to 1. The measurement values for the activity of the test promoters are corrected taking into consideration the number of molecules (per bombardment).

Calculation of the Relative Promoter Activity

The example which follows shows an example of individual calculation steps to clarify this further. The data refer to a study on the quantification of the relative promoter activity of the A-subunit promoter (70 kD) of the *Beta vulgaris* V-type H$^+$-ATPase (test promoter, plasmid: pBVA-70/LUC). The CaMV 35S promoter (plasmid: PCaMVLN) was used as reference (standard promoter). Both test plasmids carry the luciferase structural gene (LUC). To record the transformation efficiency, the calibration plasmid pFF19G was used in the cotransformation. It carries the β-glucuronidase structural gene (GUS) under the control of the enhanced 35S CaMV promoter.

The following combinations of test plasmid× calibration plasmid were employed:

1. Test promoter: 70 kD UE-ATPase (pBVA-70/LUC)× CaMV d35S (pFF19G)

2. Standard promoter: CamV 35S (PcAMVLN)×CaMV d35S (pFF19G)

TABLE 1a

Calculation of the relative luciferase activity for the promoter construct of the 70 kD subunit of *Beta vulgaris* V-type H$^+$-ATPase (70 kD UE ATPase/LUC × CaMV d35S/GUS)

| Plate | LUC activity LU | LUC activity (−BV) LU | GUS activity LU | GUS activity (−BV) LU | Efficiency rLU | Relative LUC activity rLU | Mean rLU |
|---|---|---|---|---|---|---|---|
| 1 | 8070 | 7967 | 28734 | 22286 | 0.65 | 12257 | |
| 2 | 10977 | 10874 | 40238 | 33790 | 0.99 | 10984 | |
| 3 | 13834 | 13731 | 40640 | 34192 | 1 | 13731 | 12324 |

Background activity: The absolute values obtained from the determination of the enzyme activity (LUC and β-GUS activity) of transformed cells were corrected by taking into consideration the measurement values of the negative control (absolute value−blank value (BV)). The blank value for the LUC activity was 103 LU. The blank value for the GUS activity was 6448 LU. The LU (light units) indicated refer to the quantity of protein extract employed (here: 20 μl). Transformation efficiency: the highest measurement value (GUS activity) for the internal standard CaMV d35S/GUS, and thus the highest transformation efficiency, was obtained in plate 3. The values for the LUC activities of the remaining transformation batches were corrected by taking into consideration the respective transformation efficiency.

TABLE 1b

Calculation of the relative luciferase activity for the CaMV 35S promoter (35S CamV/LUC × CaMV d35S/GUS); see legend to Table 1a

| Plate | LUC activity LU | LUC activity (−BV) LU | GUS activity LU | GUS activity (−BV) LU | Efficiency rLU | Corrected LUC activity rLU | Mean rLU |
|---|---|---|---|---|---|---|---|
| 1 | 4518 | 4415 | 13756 | 7308 | 0.21 | 21024 | |
| 2 | 13572 | 13469 | 20566 | 14118 | 0.41 | 32851 | |
| 3 | 11256 | 11153 | 17051 | 10603 | 0.31 | 35977 | 29951 |

To calculate the activity of the test promoter, the mean of the relative luciferase activity (see Table 1a) is corrected by taking into consideration the molecule number (copy factor) (see below). The relative strength of the test promoter is now expressed as the ratio between activity of the test promoter and activity of the standard promoter. In the present example, a value of 0.49 results for the relative promoter activity of the subunit A promoter of the *Beta vulgaris* V-type H$^+$-ATPase.

| Promoter | LUC activity (rLU) | Copy factor | Corrected LUC activity (rLU) | Promoter strength |
|---|---|---|---|---|
| 70 kD subunit ATPase | 12324 | 1.2 | 14789 | 0.49 |
| 35S CaMV | 29951 | 1 | 29951 | 1 |

IV. Construction of the Plasmid Constructs for the Ballistic Transformation

Figure 2:
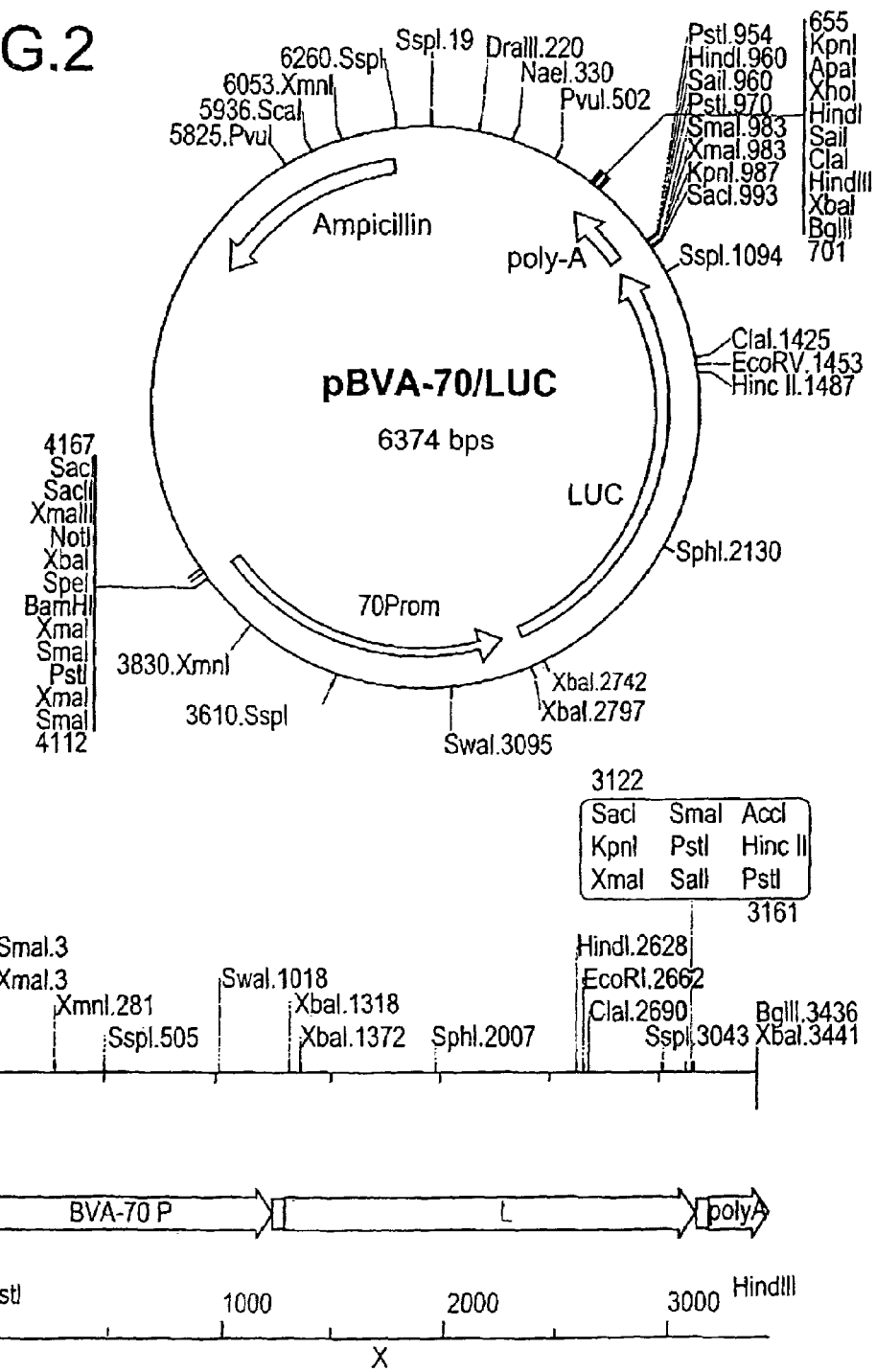
FIG. 2 shows the construction of the construct pBVA-70/LUC.

FIG. 2 shows the construction of the construct pBVA-70/LUC. To obtain the luciferase construct pBVA-70/LUC, the 5'-regulatory region (1236 bp) of the gene for subunit A of the *Beta vulgaris* V-type $H^+$-ATPase was liberated from plasmid pBVA-70 by means of a PstI/BglII digest. The genomic fragment was subsequently cloned into the vector pBluescript SKII+(Stratagene) upstream of the BamHI/HindIII cassette of vector pCaMVLN via the PstI/HindIII cleavage sites. The cassette contains the luciferase structural gene and also the polyadenylation region of nopalin synthase gene. Vector regions (■) are emphasized particularly in the BVA-70 promoter/LUC/CaMV/terminator cassette.

Figure 3:
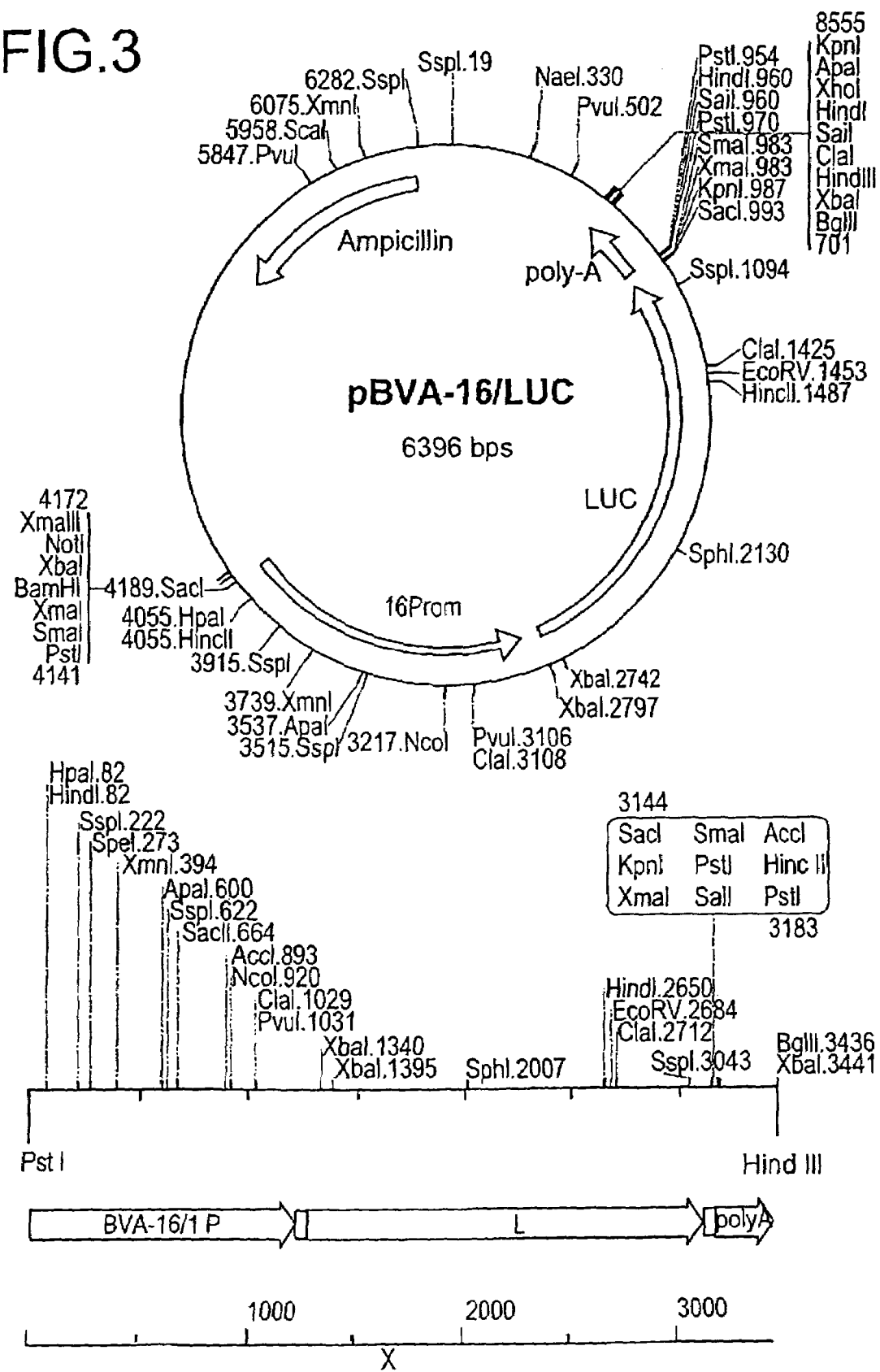
FIG. 3 shows the construction of construct pBVA-16/LUC.

FIG. 3 shows the construction of construct pBVA-16/LUC. To obtain the luciferase construct pBVA-16/LUC, the PstI/BglII fragment of the genomic subclone pBVA-16/1 (which was described in FIG. 2) was cloned into the vector pBluescript II SK+ (Stratagene) upstream of the BamHI/HindIII cassette of the vector pCaMVLN via the cleavage sites PstI/HindIII. See legend to FIG. 2.

V. Representation of the Cloned 5'-Deletions for the V-ATPase Promoters A, c1 and c2

Promoter Deletions of the BVA/16-2 Promoter/LUC Construct

The starting construct for the promoter deletions is the promoter/leader luciferase construct pBVA/16-2 LUC. This construct contains the overall promoter region with 1923 bp and additionally 87 bp of the leader (−1923 to +87=2010 bp). The ATPase promoter is to be deleted with the aid of the "Exo Mung Bean Deletion Kit" (Stratagene, 1997), starting from the 5'-end.

Figure 4:
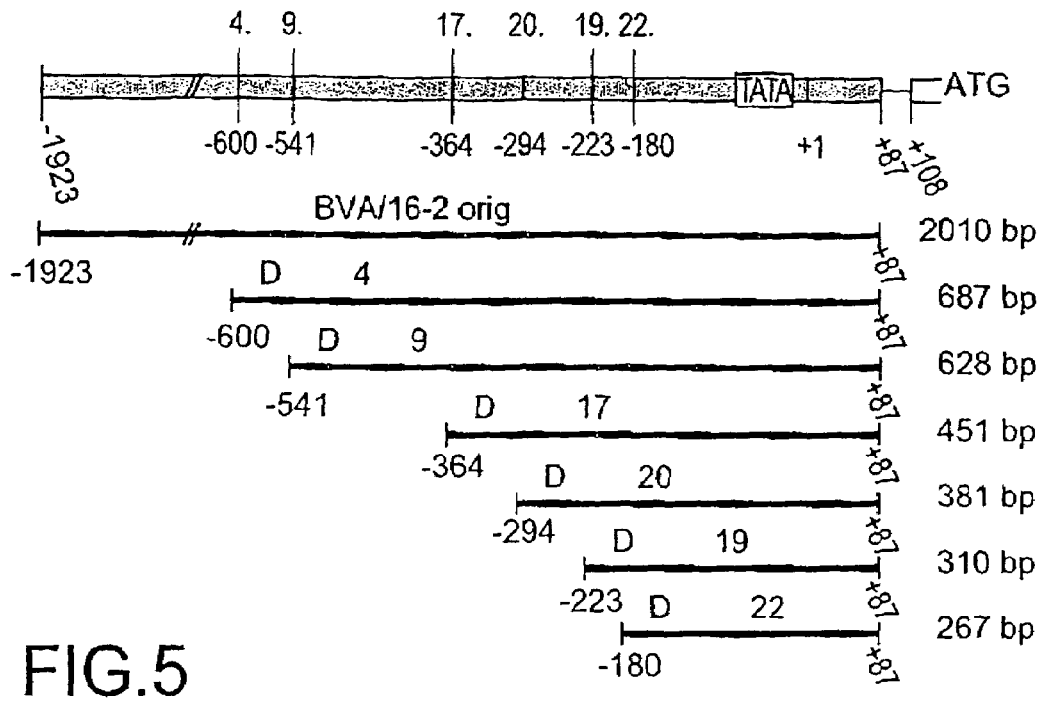
FIG. 4 shows the BVA/16-2 promoter deletions.

FIG. 4 shows the BVA/16-2 promoter deletions. The top row of the figure shows the promoter region of the original genomic clone pBVA/16-2 with the leader up to the translation start (ATG). The transcription start is shown as +1. The individual deletion clones are shown schematically underneath, and the number of the deletion clone is given. The number on the left-hand side shows the length of the remaining promoter, and the number on the right-hand side at the end of each row shows the total length of the deleted promoter and the leader portion (in each case +87 bp) in the promoter/luciferase construct.

To prevent digestion of the vector, too, a restriction cleavage site for an enzyme in the MCS on the left of the vector is selected which cleaves neither in the promoter nor in the reporter gene. A restriction enzyme with a 3'-overhang requires no fill-in reaction. In the case of a restriction enzyme with a 5'-overhang, for example NotI, the sticky end is filled up after the digest with α-thio dNTPs with the aid of Klenow polymerase. First, the 5'-end of the promoter is shortened by 1121 bp with the aid of an SpeI digest, starting at the 5-end. In the promoter/leader fragment of the construct, 812 bp of the promoter plus 87 bp of the leader=899 bp remain. The SpeI digest results in a 5'-restriction overhang. The enzyme exonuclease III digests 5'-restriction overhangs which have not been filled up with α-thio-dNTPs. After the construct has been digested with NotI, subsequently filled up with α-thio-dNTPs and then digested with SpeI, the 5'-deletion of the promoter with exonuclease III can be started (initially, 10 deletion points are chosen). The vector end of the construct remains unaltered. After the exonuclease III has been digested, the remaining overhangs are digested with mung bean nuclease. This gives rise to two smooth ends which can be ligated and subsequently transformed into *E. coli* competent cells. After plasmid isolations and subsequent test digests with SacI/XbaI, the selected plasmids are subjected to incipient sequencing (TOPLAB) with the T3 vector primer (sense primer). Starting from the MCS on the left-hand side, the overhang of the vector pBluescript II SK into the 5'-deleted promoter is sequenced. Selected deletion zones are employed in the ballistic transformation using the particle gun: No. 4 with 600 bp promoter (687 bp promoter+leader), No. 9 with 541 bp promoter (628 bp promoter+leader), No. 17 with 364 bp promoter (451 bp promoter+leader), No. 20 with 294 bp promoter (381 bp promoter+leader), No. 19 with 223 bp promoter (310 bp promoter+leader) and No. 22 with 180 bp promoter (267 bp promoter+leader).

Promoter Deletions of the BVA/16-1 Promoter/LUC Construct

In the subsequent studies, the promoter of isoform 2 of the subunit c of *B. vulgaris* V-type $H^+$-ATPase (BVA/16-2) will be compared with the promoter of the other isoform known to date (isoform 1 subunit c of *Beta vulgaris* V-type $H^+$-ATPase, BVA/16–1). Thus, the promoter/leader luciferase construct pBVA/16-1 LUC (Lehr et al. 1999) is also subjected to 5'-promoter deletions (see above). This promoter (BVA/16-1) was cloned into vector pBluescript II SK+ upstream of the BamHI/HindIII cassette of the vector pCLN (with the luciferase structural gene) as a PstI/BglII fragment. The original construct contained the entire promoter region with 1126 bp and additional 131 bp of the leader (−1126 to +131=1257 bp). Finally, the deletion clones are also subjected to incipient sequencing. A clone in which deletions are carried out as far as into the leader is generated to act as a control for the promoter deletion clones. This clone therefore only contains 51 bp (+81 to +131) of the leader upstream of the luciferase. Initially, selected deletion clones are employed in the ballistic transformation with the particle gun: No. 164 with 863 bp promoter (994 bp promoter+leader), No. 1 with 662 bp promoter (793 bp promoter+leader), No. 34 with 361 bp promoter (492 bp promoter+leader), No. 55 with 110 bp promoter (241 bp promoter+leader) and the control No. 93 with 51 bp of the leader without promoter.

Figure 5:
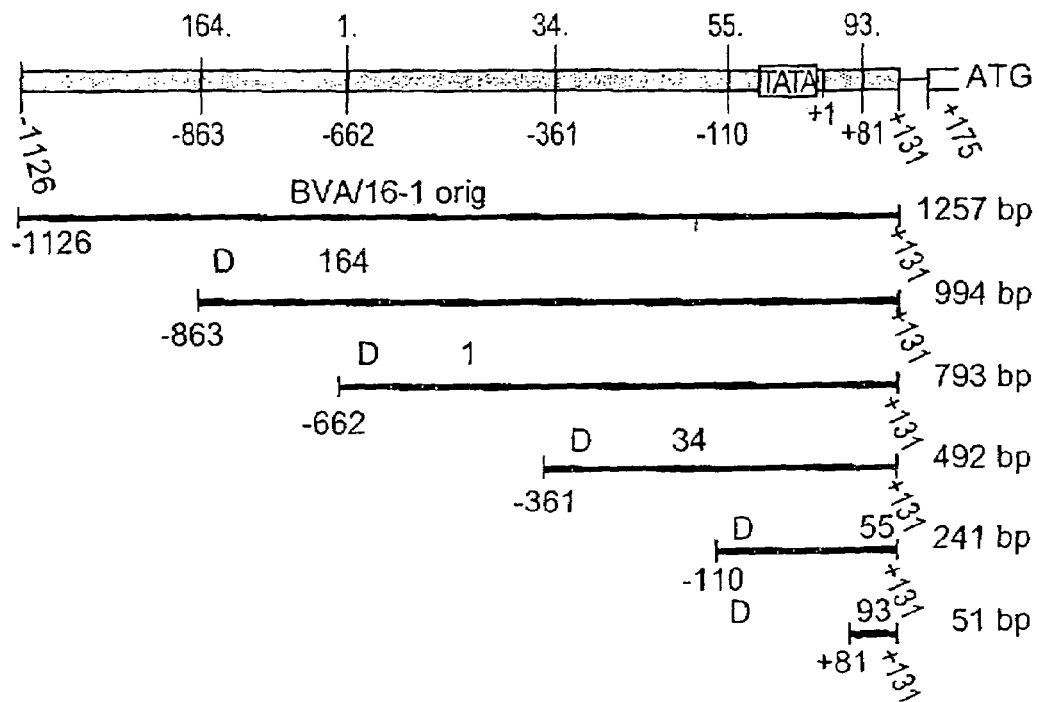
FIG. 5 shows the BVA/16-1 promoter deletions.

FIG. 5 shows the BVA/16-1 promoter deletions. The top row shows the promoter region of the original genomic clone pBVA/16-1 with the leader up to the translation start (ATG). The transcription start is shown as +1. The individual deletion clones are shown schematically underneath, and the number of the deletion clone is given. The number on the left-hand side shows the length of the remaining promoter, and the number on the right-hand side at the end of each row shows the total length of the deleted promoter and the leader portion (in each case +131 bp) in the promoter/reporter gene construct.

Deletions for the V-ATPase A Promoter

The original construct pBVA/70-LUC contained 1035 bp 5'-upstream sequence based on the transcription start. The following deletions were generated analogously to the procedure for c1 and c2:

TABLE 2

Deletion constructs of pBVA/70-LUC

| Deletion | Position based on the transcription start |
|---|---|
| d 15/47 | −30 |
| d 15/ | −108 |
| d 15/49 | −164 |
| d 13/4 | −270 |
| d 9/180 | −356 |
| s 6/80 | −494 |
| d 4/47 | −591 |

TABLE 2-continued

Deletion constructs of pBVA/70-LUC

| Deletion | Position based on the transcription start |
|---|---|
| d 4/46 | −682 |
| 7-5 LUC (= pBVA-70-LUC) | −1035 |

Figure 6:
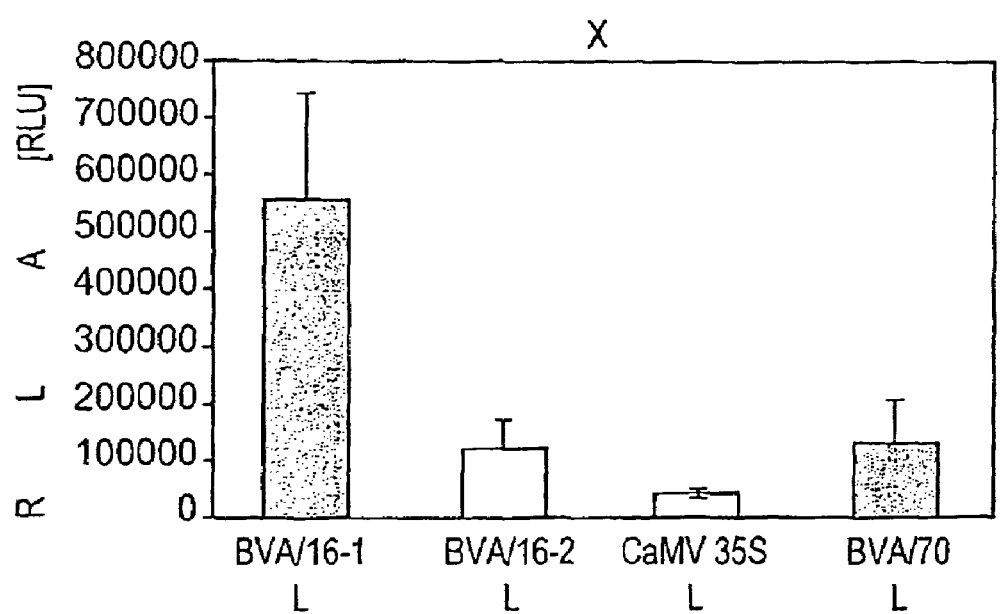
FIG. 6 shows the comparison of the activity of different promoters under control conditions.

VI. Comparison of the Promoter Activities of A, c1, c2 and CaMV35S Under Standard Conditions FIG. 6 shows the comparison of the activity of different promoters under control conditions. In this experiment with the transient gene expression by means of the ballistic transformation, the activities of the individual promoters are determined indirectly by the luciferase activity. The three V-type H[+]-ATPase promoters BVA/16-1, BVA/16-2 and BVA/70 are compared with the CaMV 35S promoter. The end values of the luciferase activities are corrected with regard to each other by a cotransformation with the construct pFF19G. The diagram shows the corrected end values with the standard deviations.

TABLE 3

End values together with promoter strengths (based on pCLN or 16-2)

| | | Luciferase activities: corrected end values [RLU] | | |
|---|---|---|---|---|
| 1. | pBVA/16-1 LUC pFF19G (1:1) | 561355 | 14.06 | 4.64 |
| 2. | pBVA/16-2 LUC pFF19G (1:1) | 120958 | 3.03 | 1 |
| 3. | pCLN pFF19G (1:1) | 39912 | 1 | |
| 4. | pBVA/70 LUC pFF19G (1:1) | 134384 | 3.36 | |

In this experiment under control conditions, the V-ATPase BVA/16-1 promoter is approximately 5 times more active than the BVA/16-2 promoter. The promoters BVA/16-2 and BVA/70 show comparable activities (the activity of BVA/70 is slightly greater than that of BVA/16-2). In comparison with the CaMV 35S promoter in the construct pCLN, the V-ATPase promoters BVA/16–2 and BVA/70 are approximately 3 times more active, and the strongest of these three ATPase promoters, BVA/16-1, shows an activity which is 14 times higher than that of pCLN.

Detection of the Constitutive Activity of the V-ATPase Promoters for the Isoforms c1 and c2 in Beta vulgaris Leaves The activities of the promoter/reporter gene constructs for c2 (full-length promoter) and c1 (5'-deletion d164) were determined by particle bombardment on fully expanded leaves of plants which have been raised in the field. To this end, in each case 2 leaf disks (Ø 5 cm) one on top of the other in Petri dishes on moist paper filters were bombarded with the particle gun (1 bursting disk, 900 psi). Bombardment with 0.5 µg of plasmid (V-ATPase promoter/pFF19G=7.3). After the bombardment, the leaf disks were incubated for 24 hours in the light while floating on water in Petri dishes.

TABLE 4

Detection of the constitutive activity of the V-ATPase promoters for the isoforms c1 and c2 in Beta vulgaris leaves

| Promoter | Experiment No. | LUC activity |
|---|---|---|
| CaMV 35S | 1 | 2348 |
| | 2 | 829 |
| | 3 | 832 |
| c1 (d164) | | 565 |
| | | 527 |
| | | 534 |
| c2 | | 1691 |
| | | 1404 |
| | | 669 |

The results in Table 4 demonstrate that the promoters c2 and c1 (d164) show activities which are comparable with CaMV 35S, even in fully expanded leaves. In parallel, a Northern blot analysis revealed that, as has already been shown for c1, the c2 isoform is also expressed constitutively in the root, in young leaves and in old leaves, as expected. As has already been described for c1 (Lehr et al. 1999), salt stress of the plants results in an increased amount of transcript.

Northern Blot Analysis on the Expression of the c2 Isoform in Beta vulgaris

Figure 7:
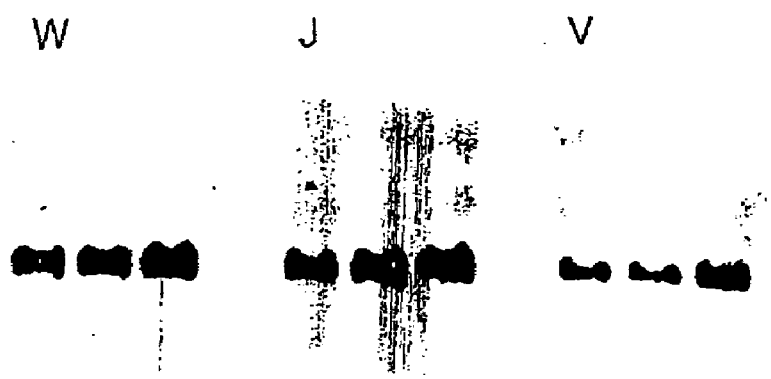
FIG. 7 shows a Northern blot analysis on the expression of the c2 isoform in *Beta vulgaris*.

FIG. 7 shows a Northern blot analysis on the expression of the c2 isoform in Beta vulgaris. In each case, 10 µg of total RNA were applied and hybridized with a gene-specific probe from the 3-UTR region. In each case two samples from control plants (left, center) and one sample from salt-treated plants (100 mM, 48 hours; right) were applied.

Figure 8A:
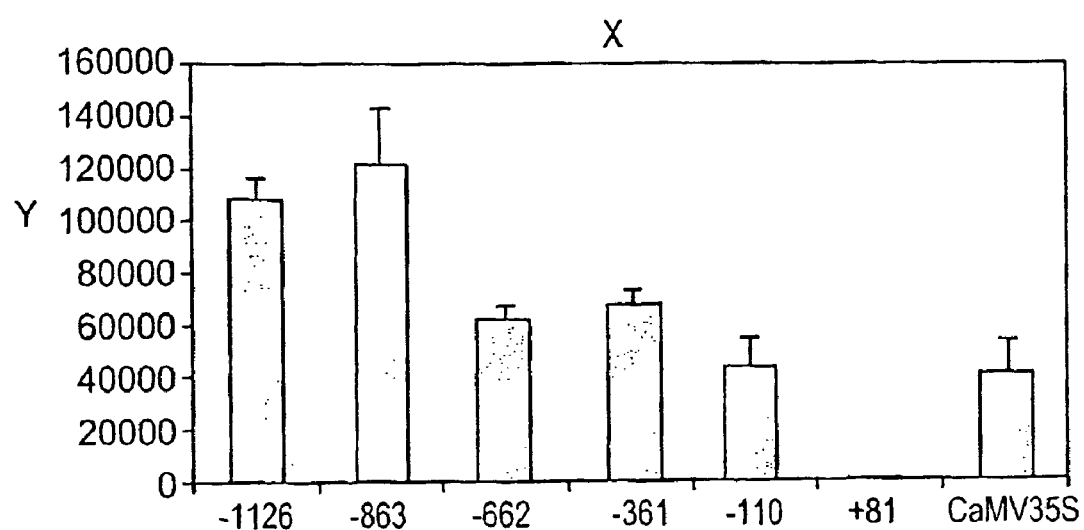
FIGS. 8a and 8b show the comparison of the activities of different deleted promoters under control conditions.
Figure 8B:
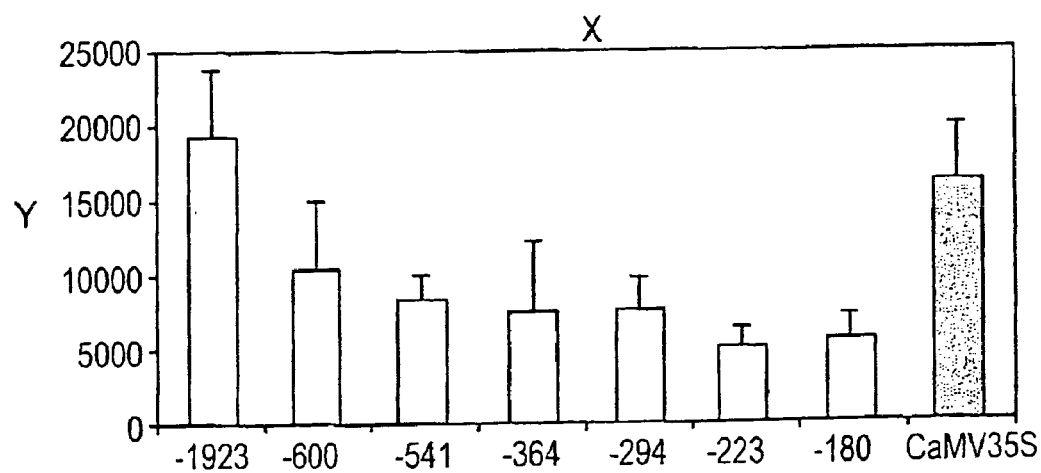

VII. Relative Activities of 5'-Deletions of the Promoters A, c1 and c2 in Comparison to CaMV35S FIGS. 8A and 8B show the comparison of the activities of different deleted promoters under control conditions. In this experiment with the transient gene expression by means of the ballistic transformation, the activities of the individual promoters are determined indirectly by the luciferase activity. The deleted V-type H'-ATPase promoters BVA/16-1 and BVA/16-2 are compared with the CaMV 35S promoter. The end values of the luciferase activities are corrected with regard to each other by a cotransformation with the construct pFF19G. The diagram shows the corrected end values with the standard deviations. The numbers beneath the columns refer to the various deletion fragments shown in FIGS. 4 and 5.

Promoter Activities of Various 5'-Deletions of the V-ATPase A Promoter in Comparison to the CaMV 35S Promoter

TABLE 5

Comparison of the activities of various deleted promoters of the V-ATPase promoter of subunit A under control conditions

| Promoter | LUC activity |
|---|---|
| CaMV 35S | 48766 |
| 70-5LUC (−1035) (full-length promoter) | 93459 |
| d4/46 (−682) | 90716 |
| d4/47 (−591) | 89906 |
| d6/80 (−494) | 62572 |
| d9/180 (−356) | 56545 |
| d13/14 (−270) | 77619 |
| d15/49 (−164) | 43623 |
| d15/7 (−108) | 43046 |
| d15/479 (−30) | 44448 |

Table 5 shows the comparison of the activities of different deleted promoters of the V-ATPase promoter of subunit A under control conditions. In this experiment with the transient gene expression by means of the ballistic transformation, the activities of the individual promoters are determined indirectly by the luciferase activity. The deleted V-type $H^+$-ATPase promoters of BVA/70 are compared with the CaMV 35S promoter. The end values of the luciferase activities are corrected with regard to each other by a cotransformation with the construct pFF19G. The diagram shows the corrected end values. The numbers of the promoters indicate the various deletion fragments given in Table 3.

VIII. Promoter Activities of Various 5'-Deletions of the V-ATPase c1 Promoter and of the CaMV 35S Promoter During the Grown of a Beta Cell Culture Table 6 shows the Promoter activities of various 5'-deletions of the V-ATPase c1 promoter and of the CaMV 35S promoter during the grown of a Beta cell culture. The activities were determined in Beta suspension cells 1.5, 3.5, 5.5 and 7.5 days after they were transferred to fresh medium.

TABLE 6

Promoter activities of various 5'-deletions of the V-ATPase c1 promoter and of the CaMV 35S promoter during the growth of a *Beta* cell culture

| Days after transfer | Promoter activities (LUC) | | | |
|---|---|---|---|---|
| | CaMV 35S | d5/55 (−110) | d3/34 (−361) | d0/164 (−863) |
| 1.5 | 75141 | 51857 | 106816 | 165252 |
| 3.5 | 75170 | 59147 | 132474 | 219219 |
| 5.5 | 63916 | 44955 | 108072 | 157218 |
| 7.5 | 18192 | 16954 | 31877 | 51930 |

IX. Effect of NaCl(KCl) Stress on the Promoter Activities of A, c1, c2 and CaNV35S Effect of NaCl (KCl Stress (125 mM/48 Hours) on the Activities of a 5'-Deletion of the A Promoter (d4/46 [−682 bp]) and a 5'-Deletion of the c1 Promoter (d164 [−863]) in Beta Cell Cultures 1.5 days after the last transfer, the cells were suction-filtered on filter paper disks and incubated on Petri dishes with control medium or with addition of 125 mM NaCl (KCl). After the bombardment, they were incubated for a further 24 hours. Then, the LUC activities were determined.

TABLE 7

Effect of NaCl or KCl stress on the activities of the V-ATPase promoters

| Promoter | LUC activity | | |
|---|---|---|---|
| | Control | +125 mM NaCl | +125 mM KCl |
| CaMV35S | 32527 (100) | 8384 (26) | 4711 (14) |
| d164 (c1) | 67841 (100) | 51380 (76) | 22379 (33) |
| CaMV35S | 20924 (100) | 5036 (24) | n.d. |
| d4/46 (A) | 23165 (100) | 9886 (43) | n.d. |

The results demonstrate that the activities of the V-ATPase promoters are considerably less affected by NaCl or KCl stress of the cells than the CaMV35S promoter. Further information on this can be found in Lehr et al. (1999).

Figure 9C:
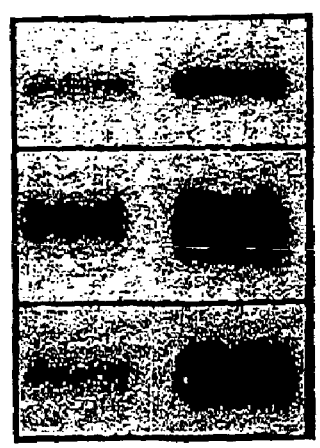
FIG. 9 shows the Northern blot analysis that the transcript quantities for the V-ADTase genes A, c1 and c2 after exposure to salt are all elevated compared with the control treatment.
Figure 9A:
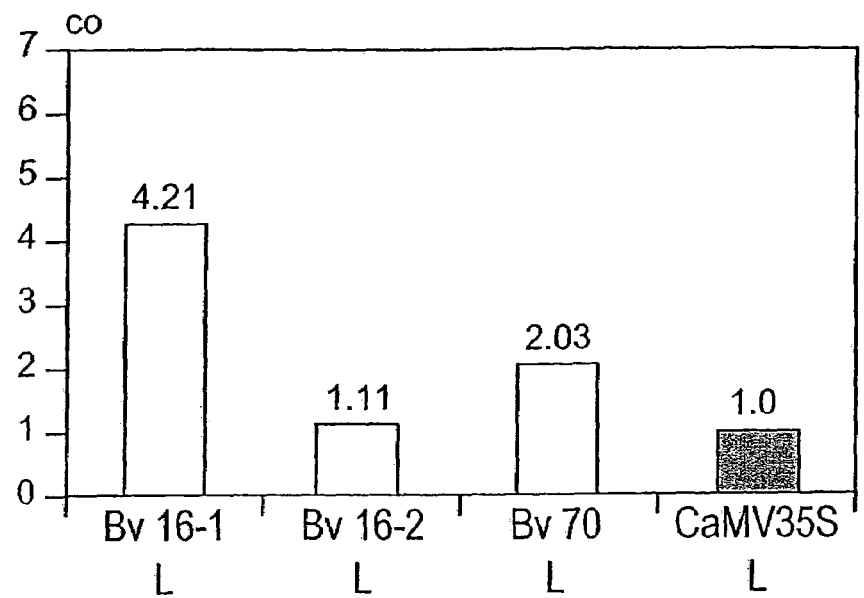
Figure 9B:
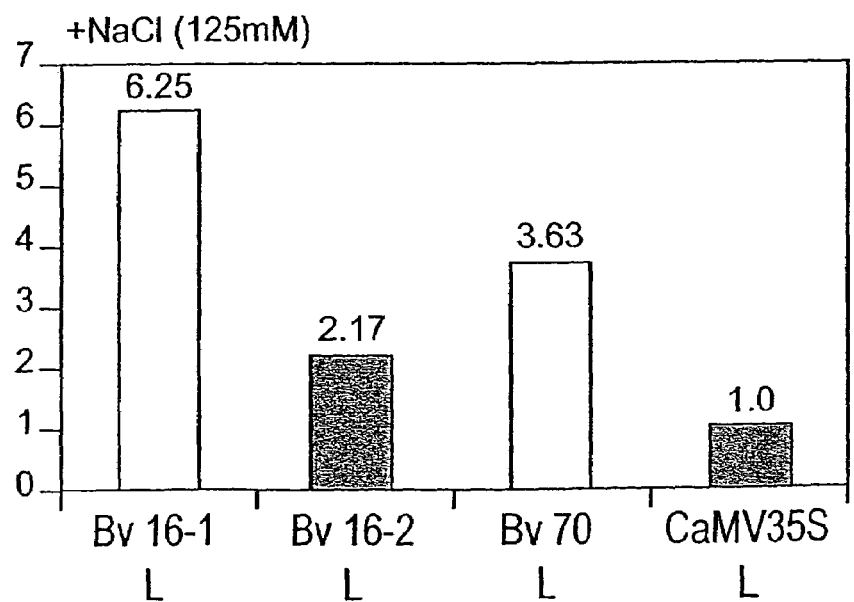

FIG. 9 demonstrates that the comparable effect is also observed for the c2 promoter. The data shown are the activities after exposure to 125 mM NaCl for at least 24 hours. Also, FIG. 9, at the bottom, shows in the Northern blot analysis that the transcript quantities for the V-APTase genes A, c1 and c2 after exposure to salt are all elevated compared with the control treatment.

X. Effect of Phosphate Deficiency on the Promoter Activities of A, c1, c2 and CaMV35S Effect of Phosphate Deficiency (48 Hours) on the Activities of a 5'-Deletion of the A Promoter (d4/46 [−682 bp]) and a 5'-deletion of the c1 promoter (d164 [−863]) in Beta cell cultures 1.5 days after the last transfer, the cells were suction-filtered onto filter paper disks and these were incubated on Petri dishes for 48 hours either in control medium or in phosphate-free medium. After the bombardment, they were incubated for a further 24 hours. Then, the LUC activities were determined.

TABLE 8

Effect of phosphate deficiency (48 hours) on the activities of a 5'-deletion of the A promoter (d4/46 [−682 bp]) and a 5'-deletion of the c1 promoter (d164 [−863]) in *Beta* cell cultures

| Promoter | LUC activity Control (+P) | − Phosphate |
|---|---|---|
| CaMV35S | 33084 (100) | 6842 (20) |
| d164 (c1) | 97417 (100) | 32897 (34) |
| CaMV35S | 20924 (100) | 2678 (13) |
| d4/46 (A) | 23165 (100) | 7406 (32) |

The results demonstrate that the activities of the V-ATPase promoters are markedly less affected by phosphate deficiency of the cells than the activity of the CaMV35S promoter.

XI. Effect of Sucrose Deficiency on the Promoter Activities of A, c1, c2 and CaMV35S Effect of Sucrose Deficiency (48 Hours) on the Activities of a 5'-Deletion of the A Promoter (d4/46 [−682 bp]) and a 5'-Deletion of the c1 Promoter (d164 [−863]) in Beta Cell Cultures 1.5 days after the last transfer, the cells were suction-filtered onto filter paper disks and these were incubated on Petri dishes for 48 hours either in control medium or in sucrose-free medium. After the bombardment, they were incubated for a further 24 hours. Then, the LUC activities were determined.

TABLE 9

Effect of sucrose deficiency (48 hours) on the activities of a 5'-deletion of the A promoter (d4/46 [−682 bp]) and a 5'-deletion of the c1 promoter (d164 [−863]) in *Beta* cell cultures

| Promoter | LUC activity Control (+S) | − Sucrose |
|---|---|---|
| CaMV35S | 33084 (100) | 31740 (95) |
| d164 (c1) | 97417 (100) | 71017 (73) |
| CaMV35S | 20924 (100) | 6933 (33) |
| d4/46 (A) | 23165 (100) | 6780 (29) |

The results demonstrate that sucrose deficiency of cells affects the activities of the V-ATPase promoters to a similar extent as the activity of the CaMV35S promoter.

XII. Coordinated Wound Induction of the V-ATPase Genes A, c1, C2 and E in Storage Tissue of Beta Beet Expression of V-ATPase and V-PP$_i$ase Genes After Wounding To detect the steady-state transcript levels of the V-PP$_i$ase and various V-ATPase subunits from the head, stalk and membrane-integral region, samples were taken at various points in time after wounding. After the RNA was isolated, a Northern blot was carried out in which 15 µg of RNA were applied per point in time. The same blot was developed repeatedly in succession with different homologous biotin-labeled probes. To detect the transcripts of the two isoforms of proteolipid c, the gene-specific c1 probe was stripped from the membrane after detection before hybridization with the gene-specific c2 probe took place. As can be seen from FIG. 10, the c1 probe was not stripped completely; the bands of the slightly larger transcript of the isoform c1 can still be recognized weakly above the signals of isoform c2, which, however, demonstrates that the mRNAs of the isoforms were indeed detected specifically. Since the transcripts of the A subunit and of the V-PP$_i$ase also migrate over a similar distance in the gel, the membrane was again stripped between the detection of the mRNA for the A subunit and for the V-PP$_i$ase.

Figure 10:
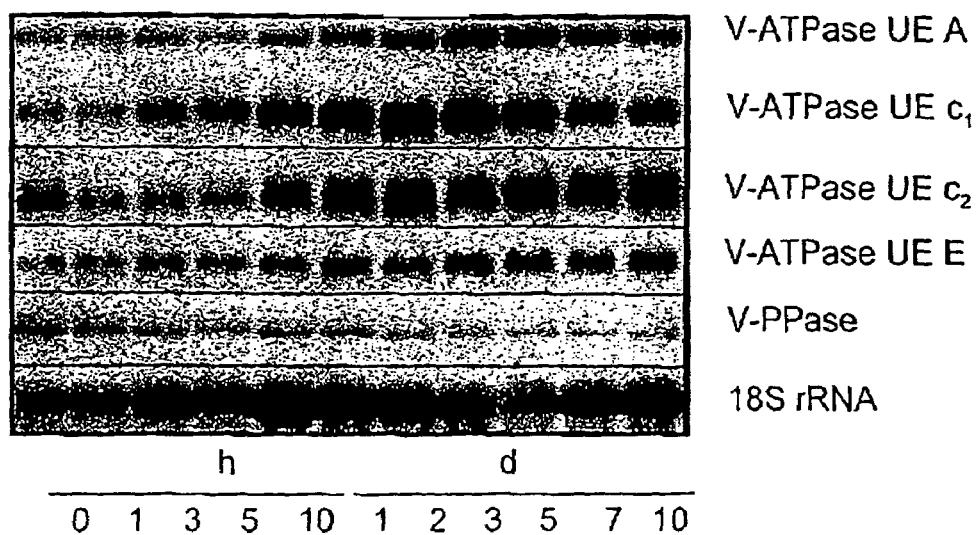
FIG. 10 shows the Northern blot analysis for detecting the gene expression of V-ATPase and V-PP$_i$ase in storage parenchyma cells of sugar beet after mechanical wounding.

The storage root of sugar beet is a tissue which requires a great deal of energy supply to the tonoplast in order to maintain its sucrose storage capacity. FIG. 10 shows that indeed both proton pumps in the vacuoles show a significant basal expression, as can be expected after staining with neutral red.

FIG. 10 shows the Northern blot analysis for detecting the gene expression of V-ATPase and V-PP$_i$ase in storage parenchyma cells of sugar beet after mechanical wounding. In each case 15 µg of RNA were applied.

Wound-Induced Changes in V-ATPase at the Protein Level

A Western blot analysis is chosen to test if the elevated transcription levels of a large number of V-ATPase genes which are observed after wounding in Northern blots are also reflected in elevated protein quantities. Membrane proteins and the enriched tonoplast fraction as well as the total microsome fraction, all of which had been isolated 0, 10 and 72 hours after wounding, were fractionated by electrophoresis in a 13% PAA gel and blotted onto a PVDF membrane. The membrane was subsequently developed with the antiserum against the *K. daigremontiana* V-ATPase holoenzyme. It emerged that no significant quantitative change in the V-ATPase subunits is observed in the total microsome fraction (FIG. 11B). In the enriched tonoplast fraction, too, the protein quantities of the subunits clearly remain constant after wounding, with one exception: subunit c, whose isoforms had also shown the strongest induction at the mRNA level, was markedly increased after wounding. This induction was equally strong in the enriched tonoplast fractions of two beets which were isolated independently of each other (FIG. 11A).

Figure 11:
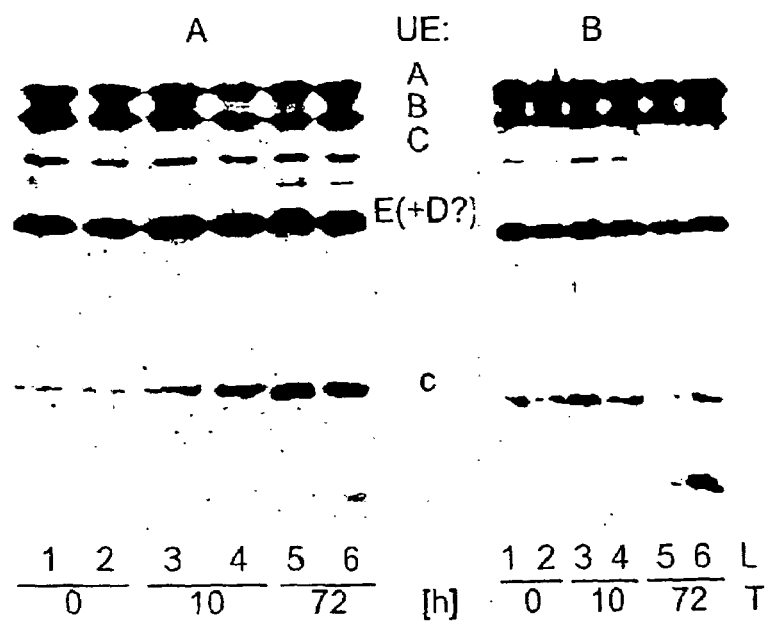
FIG. 11 shows the Western blot analysis with a polyclonal antiserum against the *K. daigremontiana* V-ATPase holoenzyme and shows wound-induced changes in V-ATPase on the tonoplast in the storage parenchyma of the sugar beet.

FIG. 11 shows the Western blot analysis with a polyclonal antiserum against the *K. daigremontiana* V-ATPase holoenzyme and shows wound-induced changes in V-ATPase on the tonoplast in the storage parenchyma of the sugar beet. A. After wounding, the subunit c protein quantity increases in the enriched tonoplast fraction as a function of time. B. In the total microsome fraction, the quantities of the individual subunits remain unchanged. In each case 5 µg of protein of the isolated membranes of two sugar beet were applied, beet 1: tracks 1, 3 and 5; beet 2: tracks 2, 4 and 6.

Reduced V-ATPase H$^+$-Pump Activity After Wounding

As has been described in the above chapters, an induction at the mRNA level was found for several V-ATPase genes, and an elevated subunit c protein level on the tonoplast was found by Western blot analysis, after wounding. This gave rise to the question of whether these changes would also lead to an elevated proton pump performance of the V-ATPase. To study this, the H$^+$-pump activity of isolated membrane vesicles of the microsomal and of the enriched tonoplast fraction in the presence of the inhibitors vanadate for P-ATPases and azide for F-ATPases was measured by means of the fluorescent dye acridine orange. Instead of sucrose, the pump medium contained 250 mM sorbitol to exclude effects caused by the H$^+$ sucrose antiporter.

Figure 12:
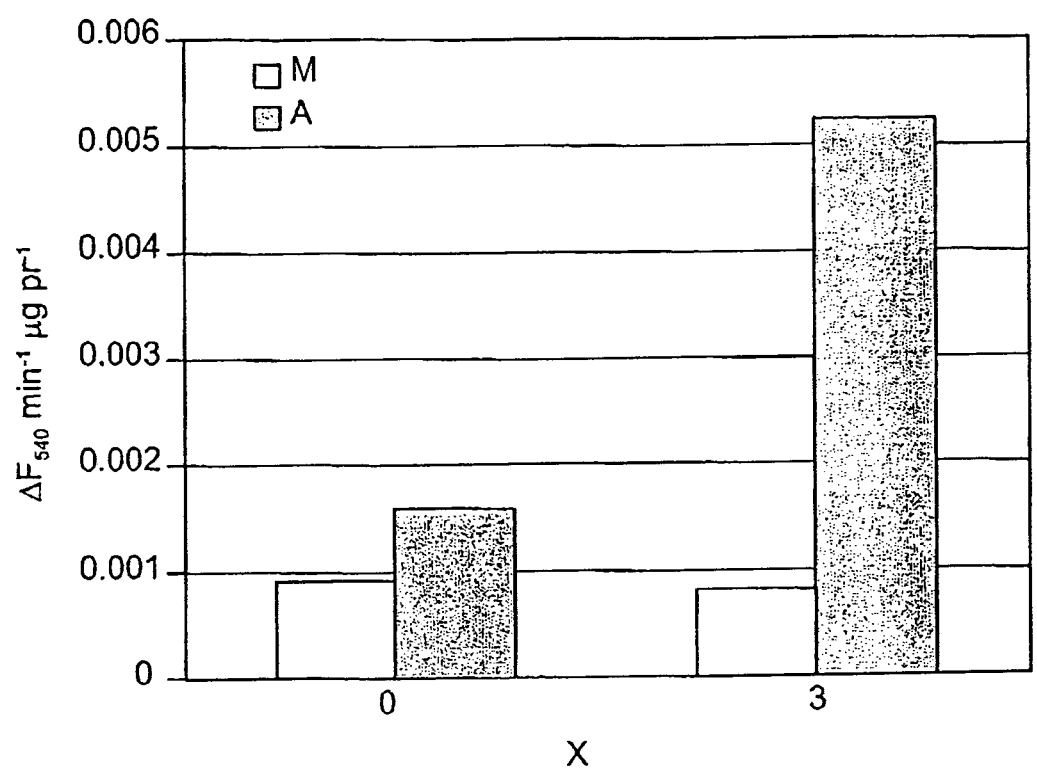
FIG. 12 shows wound-induced changes in the H$^+$-pump activity of the V-ATPase in the microsomal and in the enriched tonoplast fraction in the presence of 100 µM vanadate and 1 mM azide.

As shown in FIG. 12, the H$^+$-pump activity of the V-ATPase in the microsomal fractions is equally high before and after wounding. In contrast, 3 days after wounding, the proton pump activity in the enriched tonoplast fraction is increased by a factor of 3.3.

Accordingly, the protein levels of proteolipid c on the tonoplast (FIG. 12), which are elevated after wounding, are accompanied by a significantly elevated H$^+$-pump activity of the V-ATPase localized therein.

FIG. 12 shows wound-induced changes in the H$^+$-pump activity of the V-ATPase in the microsomal and in the enriched tonoplast fraction in the presence of 100 µM vanadate and 1 mM azide. While the initial rate of the decrease in fluorescene ($\Delta$F540) of acridine orange after addition of 1 mM MgATP to vesicles of the microsomal fraction (40 µg of protein) is equally high before and after wounding, the enriched tonoplast fraction (10 µg of protein) shows an increase by a factor of 3.3. The data shown are the means of in each case 3 individual measurements.

We claim:

1. A DNA construct comprising the promoter of the *B. vulgaris* V-ATPase subunit c in isoform 2 SEQ ID NO: 1, operatively linked with a heterologous gene.

2. The DNA construct as claimed in claim 1, which additionally comprises a second promoter which can be regulated in a different manner than the first promoter.

3. The DNA construct as claimed in claim 1, which is an expression cassette.

4. A polynucleotide comprising the sequence of the promoter of *B. vulgaris* V-ATPase subunit c isoform 2 set forth in SEQ ID NO: 1.

5. A recombinant vector which additionally comprises the construct as claimed in claim 1.

6. The recombinant vector as claimed in claim 5, which is a shuttle vector.

7. The recombinant vector as claimed in claim 5, which is an expression vector.

8. A microorganism which is transformed with the recombinant vector as claimed in claim 5.

9. A transgenic plant cell or transgenic protoplast whose genome encompasses the DNA construct as claimed in claim 1.

10. The transgenic plant cell or transgenic protoplast as claimed in claim 9 obtained from a monocotyledonous plant.

11. The transgenic plant cell or transgenic protoplast as claimed in claim 9 obtained from a dicotyledonous plant.

12. A transgenic plant whose genome additionally comprises the construct as claimed in claim 1.

13. The transgenic plant as claimed in claim 12, which is a monocotyledonous plant.

14. The transgenic plant as claimed in claim 12, which is a dicotyledonous plant.

15. The transgenic plant as claimed in claim 12, which is sugar beet, tobacco, barley, rice, potato, sunflower, soya, tomato, Canola, wheat, oilseed rape, sorghum, carrot, maize, Mesemranthemum crystallinum or *Arabidopsis thalinana*.

16. A method of producing a recombinant protein in a plant cell or a protoplast comprising the steps of transforming said plant cell or protoplast with the DNA construct as claimed in claim 1 and of expressing said DNA construct in those plant cells or protoplasts, wherein the recombinant protein is produced by means of said DNA construct.

17. A method of producing a recombinant protein in a plant comprising the step of transforming said plant with the DNA construct as claimed in claim 1, and of expressing said DNA construct in the plant, wherein the recombinant protein is produced by means of said DNA construct.

18. A method for the expression of a heterologous gene, in a plant cell or a protoplast, which comprises transforming the cell or the protoplast with the DNA construct as claimed in claim 1 and subsequently exposing the transformed cell or the protoplast to a condition of salt-induced stress.

19. The method as claimed in claim 18, wherein the plant cell or the protoplast is obtained from a monocotyledonous plant.

20. The method as claimed in claim 18, wherein the plant cell or the protoplast is obtained from a dicotyledonous plant.

21. The method as claimed in claim 18, wherein the plant cell or the protoplast is obtained from sugar beet, tobacco, barley, rice, potatoes, sunflowers, soya, tomatoes, Canola, wheat, oilseed rape, sorghum, carrots, maize, *Mesembranthemum crystallinum* or *Arabidopsis thalinana*.

22. A method for the expression of a heterologous gene in a plant, which comprises regenerating cells or protoplasts transformed with the DNA construct as claimed in claim 1 to produce a transgenic plant and subsequently exposing the plant transformed in this way to a condition of salt-induced stress.

23. The method as claimed in claim 22, wherein the transgenic plant is a monocotyledonous plant.

24. The method as claimed in claim 22, wherein the transgenic plant is a dicotyledonous plant.

25. The method as claimed in claim 22, wherein the transgenic plant is sugar beet, tobacco, barley, rice, potatoes, sunflowers, soya, tomatoes, Canola, wheat, oilseed rape, sorghum, carrots, maize, *Mesembranthemum crystallinum* or *Arabidopsis thalinana*.

26. A method for producing a recombinant protein, which comprises transforming a plant cell or a protoplast with the DNA construct as claimed in claim 1 and subsequently exposing the transformed cell or the protoplast to a condition of salt-induced stress.

27. The method as claimed in claim 26, wherein the plant cell or the protoplast is obtained from a monocotyledonous plant.

28. The method as claimed in claim 26, wherein the plant cell or the protoplast is obtained from dicotyledonous plant.

29. The method as claimed in claim 26, wherein the plant cell or the protoplast is obtained from sugar beet, tobacco, barley, rice, potatoes, sunflowers, soya, tomatoes, Canola, wheat, oilseed rape, sorghum, carrots, maize, *Mesembranthemum crystallinum* or *Arabidopsis thalinana*.

30. A method of producing a recombinant protein in a plant, which comprises regenerating cells or protoplasts transformed with a DNA construct as claimed in claim 1 to produce a transgenic plant and subsequently exposing the resulting transgenic plant to a condition of salt-induced stress.

31. The method as claimed in claim 20, wherein the transgenic plant is a monocotyledonous plant.

32. The method as claimed in claim 20, wherein the transgenic plant is a dicotyledonous plant.

33. The method as claimed in claim 20, wherein the transgenic plant is obtained from sugar beet, tobacco, barley, rice, potatoes, sunflowers, soya, tomatoes, Canola, wheat, oilseed rape, sorghum, carrots, maize, *Mesembranthemum crystallinum* or *Arabidopsis thalinana*.

34. A plant cell or protoplast, which plant cell or protoplast is transformed with the DNA construct as claimed in claim 1, wherein the promoter of the DNA-construct is not repressed under a condition of salt-stress or of vulneration, or wherein said promoter shows a greater activity under a condition of salt-stress.

35. A plant cell or protoplast, which plant cell or protoplast is transformed with the DNA construct as claimed in claim 1, wherein the promoter of the DNA-construct is not repressed under a condition of salt-stress or of vulneration, or wherein said promoter shows a greater activity under a condition of salt-stress than under a condition which lacks salt-stress.

36. A plant which is transformed with the DNA construct as claimed in claim 1, wherein the promoter of the DNA-construct is not repressed under a condition of salt-stress, or wherein said promoter shows a greater activity under a condition of salt-stress than under normal conditions.

37. A plant which is transformed with the DNA construct as claimed in claim 1, wherein the promoter of the DNA-construct is not repressed under a condition of salt-stress, or wherein said promoter shows a greater activity under a condition of salt-stress than under a condition which lacks salt-stress.

* * * * *